United States Patent
Cam et al.

(10) Patent No.: US 12,329,677 B2
(45) Date of Patent: *Jun. 17, 2025

(54) SYSTEMS AND METHODS FOR MANDIBULAR ADVANCEMENT

(71) Applicant: ALIGN TECHNOLOGY, INC., San Jose, CA (US)

(72) Inventors: Bruce Cam, San Jose, CA (US); Crystal Tjhia, Sunnyvale, CA (US); Chunhua Li, Cupertino, CA (US); Vadim Matov, San Jose, CA (US); John Morton, San Jose, CA (US)

(73) Assignee: ALIGN TECHNOLOGY, INC., San Jose, CA (US)

( * ) Notice: Subject to any disclaimer, the term of this patent is extended or adjusted under 35 U.S.C. 154(b) by 80 days.

This patent is subject to a terminal disclaimer.

(21) Appl. No.: 18/480,006

(22) Filed: Oct. 3, 2023

(65) Prior Publication Data

US 2024/0024155 A1 Jan. 25, 2024

Related U.S. Application Data

(63) Continuation of application No. 17/805,153, filed on Jun. 2, 2022, now Pat. No. 11,793,667, which is a (Continued)

(51) Int. Cl.
*A61F 5/56* (2006.01)
*A61C 7/00* (2006.01)
(Continued)

(52) U.S. Cl.
CPC .............. *A61F 5/566* (2013.01); *A61C 7/002* (2013.01); *A61C 7/08* (2013.01); *A61C 7/36* (2013.01)

(58) Field of Classification Search
CPC ............ A61F 5/0102; A61F 2005/0137; A61F 2005/0139; A61F 2005/0153; A61F 5/026; A61F 5/028; A61F 2210/009; A61F 2250/0067; A61F 2/0022; A61F 2/28; A61F 2/30; A61F 2/36; A61F 2/94; A61F 5/0125; A61F 5/055; A61F 2002/9528; A61F 2250/0004; A61F 2250/0065; A61F 2/013; A61F 2/14; A61F 2/82; A61F 2/95; A61F 5/013; A61F 9/007; A61F 9/00727; A61F 5/56; A61F 2005/563; A61F 5/566;
(Continued)

(56) References Cited

U.S. PATENT DOCUMENTS 10,588,776 B2 * 3/2020 Cam ...................... A61C 7/002
11,376,153 B2 * 7/2022 Cam ...................... A61C 7/08
11,793,667 B2 * 10/2023 Cam ...................... A61C 7/002

* cited by examiner

*Primary Examiner* — Tarla R Patel
(74) *Attorney, Agent, or Firm* — FisherBroyles, LLP

(57) ABSTRACT

Improved systems, methods, and devices for treating sleep apnea are provided herein. In one aspect, an intraoral appliance for treating sleep apnea in a patient comprises an appliance shell comprising a plurality of cavities shaped to receive teeth of a jaw of the patient. The appliance shell can comprise an advancement structure arranged to interact with an opposing jaw of the patient so as to displace the lower jaw anteriorly relative to the upper jaw. The plurality of cavities can comprise cavity geometries shaped to reduce repositioning of one or more received teeth elicited by displacement of the lower jaw anteriorly relative to the upper jaw.

20 Claims, 24 Drawing Sheets

Related U.S. Application Data continuation of application No. 16/751,121, filed on Jan. 23, 2020, now Pat. No. 11,376,153, which is a continuation of application No. 14/992,325, filed on Jan. 11, 2016, now Pat. No. 10,588,776.

(60) Provisional application No. 62/161,786, filed on May 14, 2015, provisional application No. 62/103,005, filed on Jan. 13, 2015.

(51) Int. Cl.
*A61C 7/08* (2006.01)
*A61C 7/36* (2006.01)

(58) Field of Classification Search
CPC ......... A61F 5/58; Y10S 602/902; A61N 2/00; A61N 2/002; A61N 2/004; A61N 2/006; A61N 2/008; A61N 1/40; G09B 19/003; G09B 23/28; Y10T 29/49826; A61C 7/08; A61C 19/063; A61B 5/4547; A61B 5/4552; A61B 5/4557; A61B 5/682; A61B 5/0534; A63B 71/085; A63B 2071/086; A63B 2017/088
See application file for complete search history.

$(F_{net})_{naive} = (F_{net})_{uniform} = (F_{net})_{Preferential}$

SYSTEMS AND METHODS FOR MANDIBULAR ADVANCEMENT

CROSS-REFERENCE

This application is a continuation of U.S. patent application Ser. No. 17/805,153, filed Jun. 2, 2022, which is a continuation of U.S. patent application Ser. No. 16/751,121, filed Jan. 23, 2020, now U.S. Pat. No. 11,376,153, issued Jul. 5, 2022, which is a continuation of U.S. patent application Ser. No. 14/992,325, filed Jan. 11, 2016, now U.S. Pat. No. 10,588,776, issued Mar. 17, 2020, which claims the benefit of U.S. Provisional Application No. 62/161,786, filed May 14, 2015, and U.S. Provisional Application No. 62/103,005, filed Jan. 13, 2015, the disclosures of each of which are incorporated herein by reference in their entirety.

BACKGROUND

Obstructive sleep apnea (OSA) is a serious medical condition characterized by complete or partial blockage of the upper airway during sleep. The obstruction may be caused by relaxation of soft tissues and muscles in or around the throat (e.g., the soft palate, back of the tongue, tonsils, uvula, and pharynx) during sleep. OSA episodes may occur multiple times per night, thus disrupting the patient's sleep cycle. Suffers of chronic OSA may experience sleep deprivation, excessive daytime sleepiness, chronic fatigue, headaches, snoring, and hypoxia.

The use of mandibular advancement devices (also referred to as mandibular splints or mandibular advancement splints) has been proposed to treat OSA. A mandibular advancement device is an oral appliance worn in the mouth over the teeth of the upper and/or lower jaws. The device treats sleep apnea by advancing the lower jaw in an anterior direction relative to the upper jaw. This advancement tightens the tissues of the upper airway, thus inhibiting airway obstruction during sleep.

In some instances, however, existing mandibular advancement devices for treating OSA may produce undesirable side effects, such as tooth repositioning, jaw discomfort, and muscle strain. Additionally, existing approaches for designing and fabricating mandibular advancement devices may not account for or afford sufficient control over the forces applied to the patient's teeth, which may limit the degree to which such treatments can be customized for the particular patient.

SUMMARY

Improved systems, methods, and devices for treating sleep apnea are provided herein. An intraoral appliance for treating sleep apnea in a patient can be worn on a jaw of the patient and interact with the opposing jaw such that the lower jaw is displaced anteriorly relative to the upper jaw in order to treat the sleep apnea with reduced unintentional tooth movement. The intraoral appliance may comprise a plurality of tooth receiving cavities and can be configured in one or more of many ways to reduce unintentional tooth repositioning related to lower jaw displacement, such as with one or more of a thickness, a stiffness, an interior shape, a position, or an orientation of a tooth receiving cavity. The appliance may comprise a shell having a plurality of cavities shaped to receive teeth of the patient's jaw, and the plurality of cavities can be shaped to reduce and/or inhibit unintentional repositioning of one or more received teeth related to the anterior displacement of the lower jaw. The appliance can reduce unintentional repositioning with one or more of a modified force distribution on teeth, increasing anchorage of teeth, or constraining movements of teeth. The intraoral appliances having cavity geometries shaped to provide an improved distribution of the forces applied to the patient's teeth during mandibular advancement as described herein can also be beneficial for development of patient-specific treatments that balance treatment effectiveness with patient comfort. Advantageously, the appliances described herein can also incorporate cavity geometries shaped to reposition teeth in accordance with a prescribed orthodontic treatment plan, thereby allowing for the combined application of orthodontic and mandibular advancement therapies for treating sleep apnea.

Accordingly, in one aspect, an intraoral appliance for treating sleep apnea in a patient comprises an appliance shell comprising a plurality of cavities shaped to receive teeth of a jaw of the patient, wherein the appliance shell comprises an advancement structure arranged to interact with an opposing jaw of the patient so as to displace the lower jaw anteriorly relative to the upper jaw, and wherein the plurality of cavities comprises cavity geometries shaped to reduce repositioning of one or more received teeth elicited by displacement of the lower jaw anteriorly relative to the upper jaw.

In another aspect, an intraoral appliance for treating sleep apnea in a patient comprises an appliance shell shaped to receive teeth of a jaw of the patient, wherein the appliance shell comprises an advancement structure arranged to interact with an opposing jaw of the patient so as to displace the lower jaw anteriorly relative to the upper jaw, and wherein the intraoral appliance applies an amount of anterior-posterior force to the patient's teeth that is no greater than a predetermined threshold force value.

Other objects and features of the present invention will become apparent by a review of the specification, claims, and appended figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1A:
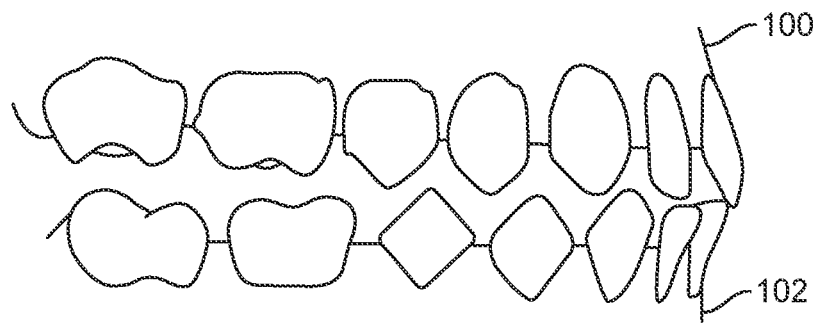
FIG. 1A illustrates a patient's upper and lower jaws in a habitual occlusal position, in accordance with embodiments.

The present disclosure provides systems, methods, and devices for treating sleep apnea (e.g., obstructive sleep apnea (OSA)) in a patient by displacing the lower jaw (mandible) of the patient anteriorly relative to the upper jaw (maxilla), also known as "mandibular advancement." The approaches described herein can be used to produce intraoral appliances for treating sleep apnea via mandibular advancement that exhibit improved control over the forces that are transmitted to the patient's teeth. In some embodiments, an appliance is designed to reduce or inhibit repositioning of teeth associated with mandibular advancement, e.g., by redistributing forces elicited by the mandibular advancement away from teeth that are more susceptible to repositioning (e.g., anterior teeth such as incisors and canines) and onto teeth that are less susceptible to repositioning (e.g., posterior teeth such as molars and premolars). In some embodiments, the appliance is configured such that the anterior-posterior force exerted on the teeth by the appliance during advancement does not exceed a predetermined amount of force, e.g., an amount that would cause tooth repositioning and/or patient discomfort. Advantageously, the force-based design approaches presented herein can be used to achieve effective, patient-specific treatment of sleep apnea while eliciting minimal or no undesirable side effects.

Thus, in one aspect, an intraoral appliance for treating sleep apnea in a patient comprises an appliance shell comprising a plurality of cavities shaped to receive teeth of a jaw of the patient. The appliance shell can comprise an advancement structure arranged to interact with an opposing jaw of the patient so as to displace the lower jaw anteriorly relative to the upper jaw. The plurality of cavities can comprise cavity geometries shaped to reduce repositioning of one or more received teeth elicited by displacement of the lower jaw anteriorly relative to the upper jaw.

In another aspect, a method for producing an intraoral appliance for treating sleep apnea in a patient comprises determining, with aid of one or more processors, a geometry of an appliance shell comprising a plurality of cavities shaped to receive teeth of a jaw of the patient. The appliance shell can comprise an advancement structure arranged to interact with an opposing jaw of the patient so as displace the lower jaw anteriorly relative to the upper jaw. The plurality of cavities can comprise cavity geometries shaped to reduce repositioning of one or more received teeth elicited by displacement of the lower jaw anteriorly relative to the upper jaw.

The cavity geometries can be designed in various ways. In some embodiments, the cavity geometries are shaped to apply a non-uniform force distribution on the one or more received teeth. The non-uniform force distribution can comprise an amount of force applied to one or more posterior teeth that is greater than an amount of force applied to one or more anterior teeth. The plurality of cavities can comprise one or more posterior cavities shaped to receive the one or more posterior teeth, and the one or more posterior cavities can comprise a position different from a position of the one or more posterior teeth. The cavity geometries can comprise a gap between an inner cavity wall and a surface of the one or more anterior teeth.

In some embodiments, the cavity geometries are shaped to increase anchorage of at least one tooth of the one or more received teeth. For example, the cavity geometries can increase the anchorage of the at least one tooth by constraining a tipping movement of the at least one tooth. As another example, the cavity geometries can increase the anchorage of the at least one tooth by applying a moment to the at least one tooth in a direction opposing a force applied to the at least one tooth by the displacement. Optionally, the plurality of cavities can comprise at least one cavity shaped to receive the at least one tooth, and the at least one cavity can comprise an orientation different from an orientation of the at least one tooth.

Some embodiments of the intraoral appliances presented herein can be configured to reposition one or more teeth as part of an orthodontic treatment regimen. In some embodiments, for example, the cavity geometries are shaped to reposition one or more received teeth from an initial tooth arrangement towards a target tooth arrangement according to an orthodontic treatment plan. The orthodontic treatment plan can comprise repositioning one or more posterior teeth in order to increase an amount of space for the patient's tongue.

In some embodiments, the approaches described herein prevent unwanted movements of anterior teeth caused by mandibular advancement treatment. For example, the plurality of cavities can be shaped to receive at least one anterior tooth, and the cavity geometries can be shaped to reduce repositioning of the at least one anterior tooth elicited by the displacement. In some embodiments, the at least one anterior tooth comprises an anterior tooth of the lower jaw and the cavity geometries are shaped to reduce anterior flaring of the anterior tooth of the lower jaw elicited by the displacement. In some embodiments, the at least one anterior tooth comprises an anterior tooth of the upper jaw and the cavity geometries are shaped to reduce retraction of the anterior tooth of the upper jaw elicited by the displacement.

Certain embodiments presented herein provide intraoral appliances designed to be worn on the upper and lower jaws. For example, the appliances described herein can further comprise a second appliance shell comprising a second plurality of cavities shaped to receive teeth of the opposing jaw. The second plurality of cavities can comprise cavity geometries shaped to reduce repositioning of one or more received teeth elicited by the displacement. The advancement structure can interact with the opposing jaw via engagement with a second advancement structure of the second appliance shell.

In some embodiments, the advancement structure comprises a first protrusion extending from the appliance shell and having a first engagement surface, and the second advancement structure comprises a second protrusion extending from the second appliance shell and having a second engagement surface configured to engage the first engagement surface. The first protrusion can be shaped to mate with the second protrusion. An inclination angle of the first and second engagement surfaces can be determined based on one or more of anatomy of the patient's jaw, kinematic data of the patient's jaw, or a targeted distance for the displacement.

In some embodiments, the advancement structure comprises a first coupling element and the second advancement structure comprises a second coupling element, the first and second coupling elements configured to interact with each other so as to reversibly bias the advancement structure and second advancement structure toward predetermined relative positions. The first and second coupling elements can comprise magnetic elements, elastic tethers, mating features, or combinations thereof, for instance.

In another aspect, an intraoral appliance for treating sleep apnea in a patient comprises an upper shell comprising a first advancement structure and a first plurality of cavities shaped to receive teeth of the patient's upper jaw, and a lower shell comprising a second advancement structure and a second plurality of cavities shaped to receive teeth of the patient's lower jaw. The first and second advancement structures can be arranged to engage each other so as to produce displacement of the lower jaw anteriorly relative to the upper jaw when the appliance is worn by the patient in order to treat the sleep apnea. At least one of the first plurality of cavities or the second plurality of cavities can comprise cavity geometries shaped to reduce repositioning of one or more received teeth elicited by the displacement.

In another aspect, a method for producing an intraoral appliance for treating sleep apnea in a patient comprises determining, with aid of one or more processors, a geometry of an upper shell comprising a first advancement structure and a first plurality of cavities shaped to receive teeth of the patient's upper jaw. The method can comprise determining, with aid of one or more processors, a geometry of a lower shell comprising a second advancement structure and a second plurality of cavities shaped to receive teeth of the patient's lower jaw. The first and second advancement structures can be arranged to engage each other so as to produce displacement of the lower jaw anteriorly relative to the upper jaw when the appliance is worn by the patient in order to treat the sleep apnea. At least one of the first plurality of cavities or the second plurality of cavities can comprise cavity geometries shaped to reduce repositioning of one or more received teeth elicited by the displacement.

In another aspect, an intraoral appliance for treating sleep apnea in a patient by displacing a lower jaw of the patient anteriorly relative to an upper jaw of the patient comprises an appliance shell shaped to receive teeth of a jaw of the patient. The appliance shell can comprise an advancement structure arranged to interact with an opposing jaw of the patient so as to displace the lower jaw anteriorly relative to the upper jaw. The intraoral appliance can apply an amount of anterior-posterior force to the patient's teeth that is no greater than a predetermined threshold force value.

In another aspect, a method for producing an intraoral appliance for treating sleep apnea in a patient comprises determining, with aid of one or more processors, a threshold force value for an amount of anterior-posterior force that would be applied to the patient's teeth in order to displace the patient's lower jaw anteriorly relative to the patient's upper jaw. The method can comprise determining, with aid of the one or more processors, a geometry for an intraoral appliance configured to displace the lower jaw anteriorly relative to the upper jaw when worn by the patient in order to treat the sleep apnea, wherein the intraoral appliance applies an amount of anterior-posterior force to the patient's teeth that is no greater than the threshold force value.

In another aspect, a system for producing an intraoral appliance for treating sleep apnea in a patient comprises one or more processors and memory comprising instructions executable by the one or more processors to cause the system to at least determine a threshold force value for an amount of anterior-posterior force that would be applied to the patient's teeth in order to displace the patient's lower jaw anteriorly relative to the patient's upper jaw. The instructions can cause the system to determine a geometry for an intraoral appliance configured to displace the lower jaw anteriorly relative to the upper jaw when worn by the patient in order to treat the sleep apnea, wherein the intraoral appliance applies an amount of anterior-posterior force to the patient's teeth that is no greater than the threshold force value.

The threshold force value can be varied as desired. In some embodiments, the threshold force value is about 20 N. The threshold force value may be no greater than an amount of anterior-posterior force associated with patient discomfort, tooth repositioning, and/or temporamandibular joint dysfunction. For example, the threshold force value can be less than an amount of anterior-posterior force that is uncomfortable for the particular patient, thus reducing or eliminating pain experienced by the patient during treatment. As another example, the threshold force value can be less than an amount of anterior-posterior force that would injure the jaw muscles and/or TMJ of the patient, in order to reduce treatment risk. In some embodiments, the threshold force value can be less than an amount of anterior-posterior force that would cause unintended movements of the jaws and/or teeth, in order to reduce the incidence of adverse side effects.

In some embodiments, the intraoral appliance comprises an upper shell comprising a first advancement structure and a first plurality of cavities shaped to receive teeth of the upper jaw, and a lower shell comprising a second advancement structure and a second plurality of cavities shaped to receive teeth of the lower jaw. The first and second advancement structures can be arranged to engage each other so as to displace the lower jaw anteriorly relative to the upper jaw. At least one of the first plurality of cavities or the second plurality of cavities can comprise cavity geometries shaped to reduce repositioning of one or more received teeth elicited by anterior displacement of the lower jaw relative to the upper jaw.

In some embodiments, the method further comprises receiving, with aid of the one or more processors, measurement data indicative of a patient-specific relationship between anterior displacement of the lower jaw relative to the upper jaw and anterior-posterior force applied to the patient's teeth. The method can further comprise determining, with aid of one or more processors, a threshold displacement value for an amount of anterior displacement of the lower jaw relative to the upper jaw corresponding to the threshold force value, wherein the intraoral appliance is configured to displace the lower jaw relative to the upper jaw by an amount no greater than the threshold displacement value.

In some embodiments, the instructions further cause the system to receive measurement data indicative of a patient-specific relationship between anterior displacement of the lower jaw relative to the upper jaw and anterior-posterior force applied to the patient's teeth. The instructions can further cause the system to determine a threshold displacement value for an amount of anterior displacement of the lower jaw relative to the upper jaw corresponding to the threshold force value, wherein the intraoral appliance is configured to displace the lower jaw relative to the upper jaw by an amount no greater than the threshold displacement value.

In another aspect, a method comprises providing an appliance in accordance with any of the embodiments presented herein.

In another aspect, a mandible advancement appliance comprises an upper jaw retainer having an upper mandibular advancement feature and a lower jaw retainer having a lower mandibular advancement feature. The upper and lower mandibular advancement features can be configured to engage each other to advance the lower jaw retainer in an anterior direction relative to the upper jaw retainer when the retainers are closed together as they would be when worn by a patient. Optionally, the upper and lower mandibular advancement features can engage each other along an engagement plane, and the angle of the engagement plane can be designed to resist the opening of the patient's jaws. An upper coupling element on the upper mandibular advancement feature and a lower coupling element on the lower mandibular advancement features can be configured to reversibly bias or "urge" the upper and lower mandibular advancement features toward preselected relative positions. The preselected relative position can include a specific degree or distance of mandibular advancement and may further include a desired degree of mouth opening or the like. Specific coupling elements can include magnets as well as reversible locking mechanisms as described in more detail below.

The upper and lower coupling elements may take any one of a variety of forms. In some embodiments, the upper and lower coupling elements comprise an upper magnetic element on the upper mandibular advancement feature and a lower magnetic element on the lower mandibular advancement feature. The upper and lower magnetic elements can be disposed on upper and lower engagement surfaces which are located on the upper and lower mandibular advancement features, respectively. Alternatively, the upper and lower coupling elements can comprise one or more elastic tethers which are connected between the upper and lower mandibular advancement features and oriented to bias the features toward the pre-selected relative positions. As a further alternative, the upper and lower coupling elements may comprise mechanical latch members which hold the mandibular advancement features at the pre-selected relative positions. For example, the mechanical latch members may comprise textured surfaces or may comprise a cup and ball.

In another aspect, a mandibular advancement system comprises a primary shell or retainer configured to removably anchor to one of a patient's upper and lower jaw and a plurality of secondary shells or retainers configured to removably anchor to the other of the patient's upper and lower jaw. The primary retainer has a mandibular advancement feature and each of the secondary retainers has a mandibular advancement feature. At least some of the mandibular advancement features on the secondary retainers can be positioned differently on the secondary retainers than are others of the mandibular advancement features on others of the secondary retainers so that a user can select a particular secondary retainer to achieve a particular degree of mandibular advancement. Such mandibular advancement systems may be used by a patient by placing the primary retainer over one jaw and a first secondary retainer over the second jaw at a first time to achieve a first degree of mandibular advancement. At a second time, the primary retainer may again be placed over the one jaw and a second secondary retainer over the second jaw. By properly selecting the second retainer, a different degree of mandibular advancement and/or mouth opening can be achieved.

In another aspect, a method for designing a mandibular advancement application for an individual patient comprises obtaining data representing the patient's tooth position and natural upper and lower jaw positions and receiving target mandibular advancement information. Design information for upper and lower jaw retainers or shells can be generated for the patient, where the design information includes at least the relative positions of upper and lower mandibular advancement features on the upper and lower retainers, respectively, and tooth engagement plans for the upper and lower retainers which favorably distribute orthodontic load minimize orthodontic load on the individual patient's teeth during use of the mandibular advancement appliance. The design information may be used to fabricate a mandibular advancement device.

It shall be appreciated that any of the embodiments herein described with reference to an upper jaw of the patient can also be applied to a lower jaw of the patient, and vice-versa. Additionally, where the upper and lower jaws are referenced in relation to each other, it is contemplated that the term "opposing" or "corresponding" can be interchangeably applied to either jaw, such any reference herein to an "upper jaw" and "opposing lower jaw" may be considered to be interchangeable with a "lower jaw" and "opposing upper jaw."

Any of the systems and methods of treatment of the present disclosure can be used with daytime retainers to avoid tooth repositioning, but it may be preferable to design the mandibular advancement appliance to avoid inducing orthodontic tooth movement in the first place.

As used herein the terms "torque" and "moment" are treated synonymously.

As used herein the term "and/or" is used as a functional word to indicate that two words or expressions are to be taken together or individually. For example, A and/or B encompasses A alone, B alone, and A and B together.

Turning now to the drawings, in which like numbers designate like elements in the various figures, FIG. 1A illustrates an upper jaw 100 and a lower jaw 102 of a patient in a habitual occlusal position, in accordance with embodiments. The habitual occlusal position can correspond to the normally closed position of the upper and lower jaws 100, 102. Patients suffering from sleep apnea may experience restricted airflow due to blockage of the upper airway if the upper and lower jaws 100, 102 remain in their habitual occlusal relationship during sleep due to relaxation of soft tissues in or around the upper airway.

Figure 1B:
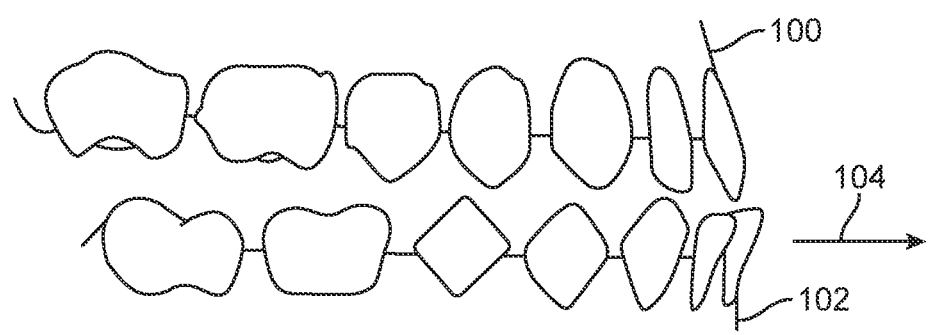
FIG. 1B illustrates a patient's upper and lower jaws in a "mandible-advanced" occlusal position, in accordance with embodiments.

FIG. 1B illustrates the upper jaw 100 and lower jaw 102 in a "mandible-advanced" occlusal position, in accordance with embodiments. In the advanced position, the lower jaw 102 has been displaced from its habitual position along an anterior direction (indicated by arrow 104) such that the lower jaw 102 is now positioned anteriorly relative to the upper jaw 100. The advanced position of the lower jaw 102 can be used to tighten the soft tissues of the upper airway, thus maintaining unobstructed airflow during sleep.

In some embodiments, an intraoral appliance is worn by the patient in the order to displace the lower jaw anteriorly relative to the upper jaw to treat sleep apnea. The intraoral appliance can be a patient-removable appliance (e.g., the patient can place and remove the appliance without aid from a practitioner) that is inserted into the patient's mouth prior to sleep so as to maintain the lower jaw in an advanced position during sleep, and is removed from the patient's mouth while the patient is awake to allow for normal activity. In alternative embodiments, the intraoral appliance can include one or more components that are not patient-removable (e.g., attachments or brackets affixed to one or more teeth, anchoring devices positioned in the tissue of the intraoral cavity such as bone).

In some embodiments, the intraoral appliance includes at least one appliance shell having a plurality of cavities shaped to receive teeth of a single jaw of the patient (e.g., the upper jaw or the lower jaw). An appliance shell can be a retainer having tooth-receiving cavities shaped to maintain the patient's teeth in a current tooth arrangement. In other embodiments, an appliance shell can be a device for tooth repositioning in which the cavities are shaped to reposition one or more received teeth from an initial arrangement to a target tooth arrangement, as described further herein. Optionally, an appliance shell can be configured to maintain some teeth in a current arrangement while repositioning others to a different arrangement, as discussed herein. The appliance can be fabricated with one or more of many materials such as metal, glass, reinforced fibers, carbon fiber, composites, reinforced composites, aluminum, biological materials, or combinations thereof. The appliance can be manufactured in many ways, such as with thermoforming or direct fabrication as described herein. Alternatively or in combination, the appliance can be fabricated with machining, such as an appliance fabricated from a block of material with computer numeric control (CNC) machining. Alternatively or in combination, additive manufacturing processes such as stereolithography or 3-D printing can be used to fabricate the appliances described herein.

A shell for an intraoral appliance can include at least one advancement structure arranged to interact with an opposing jaw of the patient, such as by directly contacting the opposing jaw, or indirectly by engaging another appliance positioned on the opposing jaw (e.g., a second shell, an attachment, an anchoring device, etc.). The interaction of the advancement structure with the opposing jaw can produce forces that displace the lower jaw anteriorly relative to the upper jaw. For example, the intraoral appliance can include an upper shell and a lower shell. Each of the upper shell and lower shell can have a set of teeth receiving cavities shaped to accommodate teeth of the upper jaw and lower jaw, respectively. The upper shell can have an advancement structure that engages a corresponding advancement structure of the lower shell when the appliance is worn by the patient so as to bring the two shells towards each other (e.g., the patient's jaws are closed). The engagement of the two advancement structures can displace the lower shell anteriorly relative to the upper shell, thereby advancing the lower jaw. Optionally, the advancement structures can constrain the movements of the upper and lower jaws with respect to up to six degrees of freedom, so as to prevent the jaws from returning to the habitual position once the advancement structures are engaged.

The design of the advancement structures described herein can be varied as desired to produce the forces for mandibular advancement. For example, an advancement structure can include protruding members, recesses, tension members (e.g., elastics, tension springs), compression members (e.g., compression springs) or combinations thereof. An advancement structure can be located on any portion of the appliance, such as on a buccal surface, lingual surface, occlusal surface, or combinations thereof. An intraoral appliance can include any number and combination of advancement structures, such as a single structure (e.g., a single structure connecting upper and lower shells), a pair of structures (e.g., paired upper and lower structures, two structures located on opposite sides of the appliance), three structures, four structures (e.g., two sets of paired upper and lower structures located on opposite sides of the appliance), or more.

Figure 2:
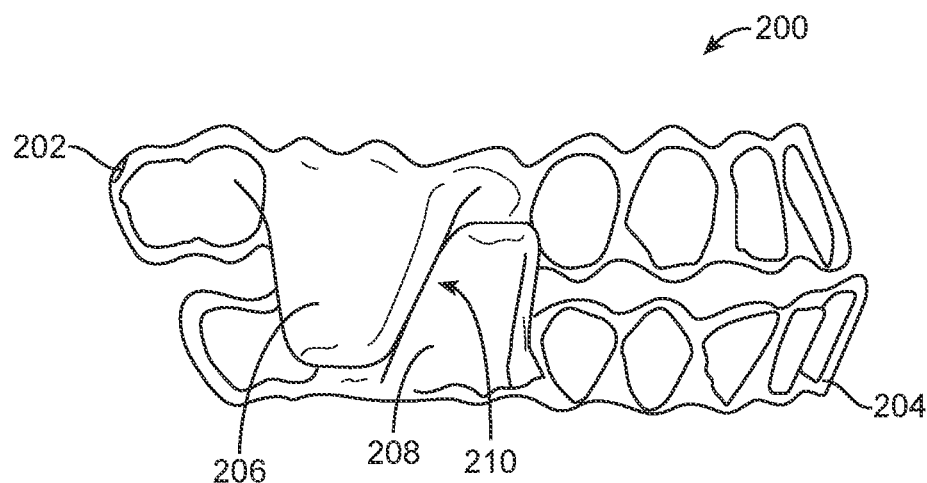
FIG. 2 illustrates an intraoral appliance for treating sleep apnea by mandibular advancement, in accordance with embodiments.

FIG. 2 illustrates an intraoral appliance 200 for treating sleep apnea by mandibular advancement, in accordance with embodiments. The appliance 200 includes an upper appliance shell 202 having a plurality of cavities for receiving teeth of the upper jaw (e.g., an upper or maxillary retainer) and a lower appliance shell 204 having a plurality of cavities for receiving teeth of the lower jaw (e.g., a lower or mandibular retainer). In some embodiments, the upper and lower shells 202, 204 each receive some or all of the anterior teeth (e.g., incisors, canines) and some or all of the posterior teeth (e.g., molars, premolars). The upper shell 202 includes an upper advancement structure 206 (e.g., a maxillary or upper mandibular advancement feature) and the lower shell 204 includes a lower advancement structure 208 (e.g., a mandibular or lower mandibular advancement feature). The upper advancement structure 206 engages the lower advancement structure 208 to displace the lower shell 204 anteriorly relative to the upper shell 202, thereby advancing the mandible when the appliance 200 is worn by the patient. Since the upper advancement structure 206 is positioned posteriorly relative to the lower advancement structure 208, engagement of the upper and lower advancement structures 206, 208 produces an anterior force that pushes the mandible in an anterior direction. Optionally, the upper and lower advancement structures 206, 208 can be arranged to prevent posterior movement of the mandible while being unrestrictive of anterior, opening, or closing movements of the mandible.

In the appliance 200, the upper advancement structure 206 is depicted as a protrusion extending downwards towards the lower jaw, and the lower advancement structure 208 is depicted as a protrusion extending upwards towards the upper jaw, such that the two protrusions contact and engage each other along an engagement region 210 when the upper and lower shells 202, 204 are brought together. For instance, the engagement region 210 can encompass a surface of the upper protrusion (e.g., an anterior surface) that engages a corresponding engagement surface of the lower protrusion (e.g., a posterior surface). Optionally, the upper and lower protrusions can have complementary shapes that mate with each other to improve the stability of engagement.

In the embodiment of FIG. 2, the upper and lower advancement structures 206, 208 are depicted as being located on the buccal surfaces of the upper and lower shells 202, 204, respectively. In alternative embodiments, the advancement structures 206, 208 can be positioned on other surfaces of the shells 202, 204, such as on the lingual surfaces or occlusal surfaces. Additionally, although FIG. 2 depicts a single pair of advancement structures 206, 208, one of ordinary skill in the art would appreciate that the appliance 200 can be modified as desired to include multiple pairs of advancement structures located at different portions of the appliance 200 (e.g., a first pair located on the left side of the appliance 200 and a second pair located on the right side of the appliance 200).

Figure 3A:
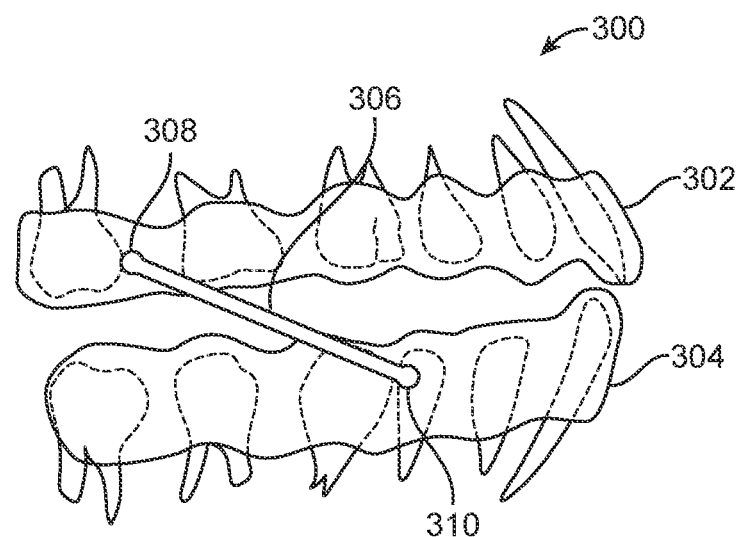
FIG. 3A illustrates an intraoral appliance for treating sleep apnea by mandibular advancement, in accordance with embodiments.

FIG. 3A illustrates an intraoral appliance 300 for treating sleep apnea by mandibular advancement, in accordance with embodiments. Similar to the appliance 200, the appliance 300 includes an upper shell 302 and a lower shell 304 having teeth-receiving cavities for the upper and lower jaws of the patient, respectively. The advancement structure of the appliance 300 is a connecting structure 306 that is coupled to the upper shell 302 at an upper anchor point 308 and to the lower shell 304 at a lower anchor point 310, thus connecting the upper and lower shells 302, 304 to each other.

Figure 3B:
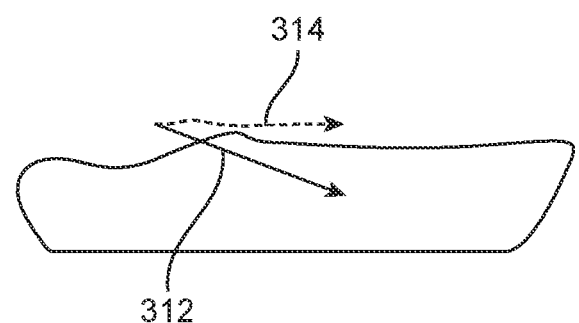
FIG. 3B illustrates an anterior force produced by the intraoral appliance of FIG. 3A.

FIG. 3B illustrates an anterior force produced by the intraoral appliance 300 of FIG. 3A. In the embodiment of FIGS. 3A and 3B, the connecting structure 306 is a compression member (e.g., a compression spring) that exerts an outward axial force 312. Since the upper anchor point 308 is positioned posteriorly relative to the lower anchor point 310, the force 312 includes an anterior force component 314 ($F_{anterior}$) that pushes the mandible in an anterior direction. In alternative embodiments, the connecting structure 306 can be a tension member (e.g., an elastic, tension spring) and the upper anchor point 308 can be positioned anteriorly relative to the lower anchor point 310, such that the inward axial force produced by the tension member would have an anterior force component to pull the mandible in an anterior direction.

Figure 4A:
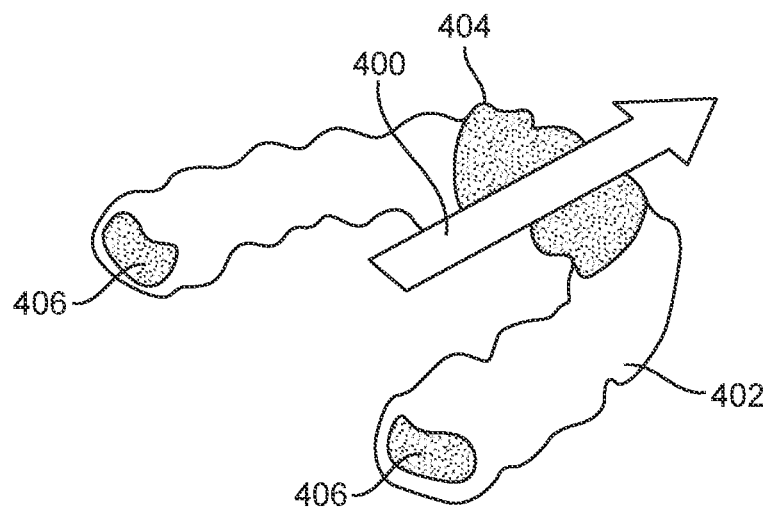
FIG. 4A illustrates exemplary tooth surfaces exposed to forces associated with mandibular advancement, in accordance with embodiments.
Figure 4B:
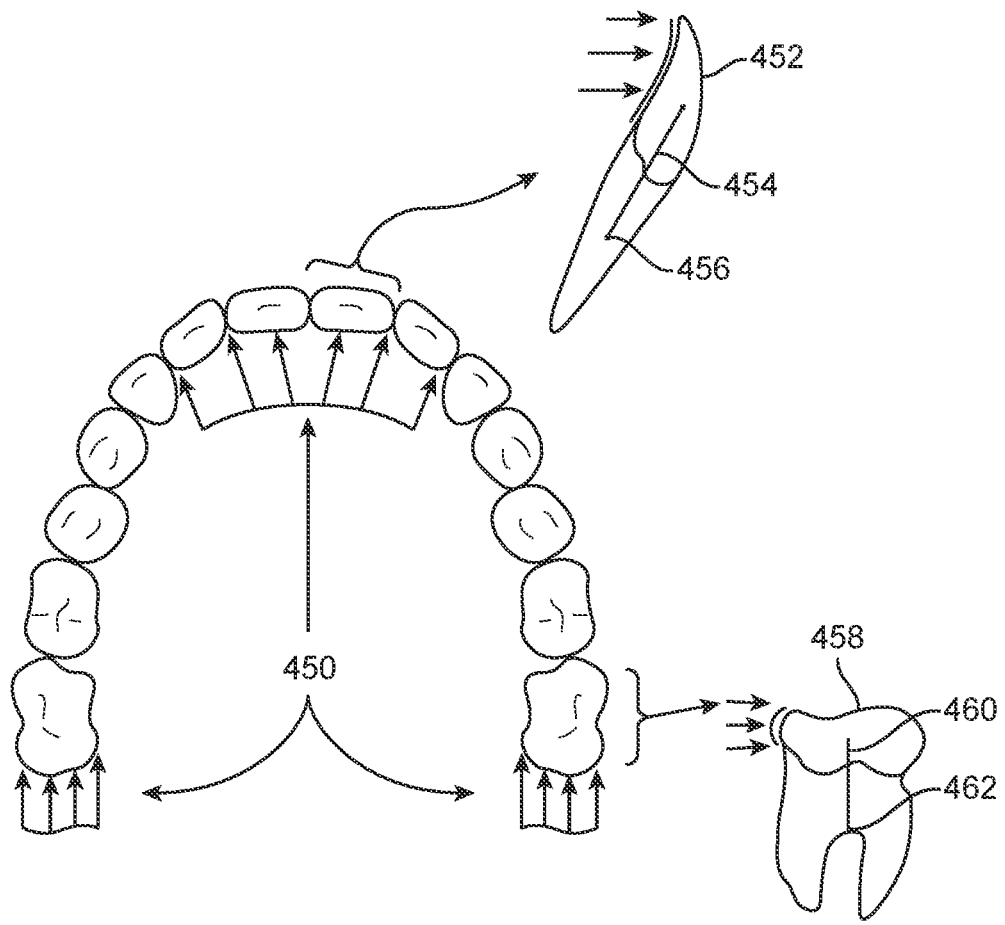
FIG. 4B illustrates a non-uniform force distribution applied on teeth during mandibular advancement.

FIGS. 4A and 4B illustrate forces applied to teeth by an intraoral appliance during mandibular advancement, in accordance with embodiments. FIG. 4A illustrates exemplary tooth surfaces exposed to a force 400 associated with mandibular advancement. An intraoral appliance can apply a net anterior (protrusive) force 400 on the patient's mandible or lower arch 402 in order to advance the mandible. The appliance can also apply a net posterior (retrusive) force on the patient's maxilla or lower arch (not shown). Teeth having more exposed surfaces orthogonal to the force direction may bear more of the applied force than teeth having less exposed orthogonal surfaces. For example, in the lower arch 402, the exposed orthogonal surfaces include the lingual surfaces of anterior teeth 404 (e.g., the lingual surfaces of the incisors) and the distal surfaces of posterior teeth 406 (e.g., the distal surfaces of the terminal molars). In the upper arch (not shown), the exposed orthogonal surfaces include the buccal surfaces of the anterior teeth (e.g., the buccal surfaces of the incisors).

FIG. 4B illustrates a non-uniform force distribution 450 applied on teeth during mandibular advancement. In the lower arch, since the lingual surface of the anterior teeth is relatively large compared to the distal surface area of the posterior teeth, the majority of the force is applied to the anterior teeth. An anterior tooth 452 (e.g., incisor) can be more susceptible to tipping, since the force applied to the tooth has a large moment arm 454 with respect to the center of resistance 456, creating a large tipping moment. In contrast, a posterior tooth 458 (e.g., molar) can be less susceptible to tipping, since the applied force has a smaller moment arm 460 with respect to the center of resistance 462. The remaining force can be distributed among the exposed surfaces of other teeth, e.g., the interproximal, buccal, lingual, and/or occlusal surfaces. The amount of force applied to these teeth can depend on the extent to which the appliance contacts and engages the teeth, as described further herein.

Figure 5:
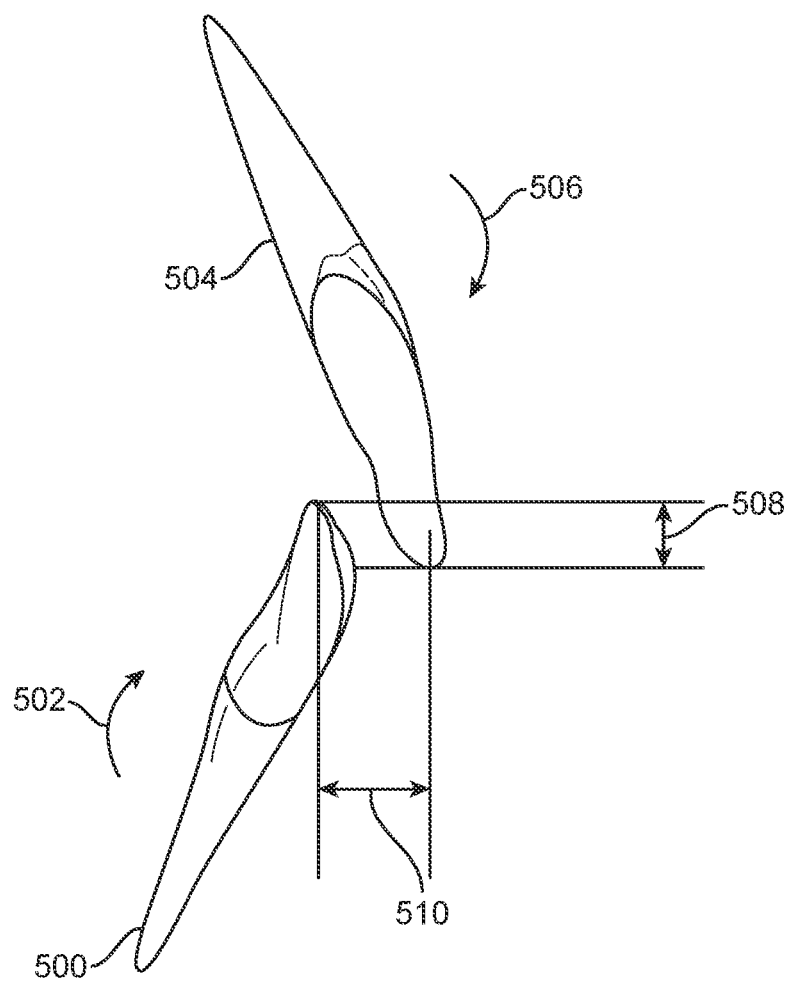
FIG. 5 illustrates repositioning of anterior teeth elicited by mandibular advancement forces, in accordance with embodiments.

FIG. 5 illustrates repositioning of anterior teeth elicited by mandibular advancement forces, in accordance with embodiments. As described herein, mandibular advancement using intraoral appliances can result in application of forces to the anterior teeth, such as anterior forces to anterior teeth of the lower jaw and posterior forces to anterior teeth of the upper jaw. For example, an anterior force applied to a lower anterior tooth 500 can cause tipping movements such as labial inclination 502, which can result in flaring or protrusion of the tooth 500. A posterior force applied to an upper anterior tooth 504 can cause tipping movements such as lingual inclination 506, which can result in retraction of the tooth 504. This repositioning of the anterior teeth can cause alterations in the patient's bite characteristics, such as a decrease in the amount of overbite 508 and/or a decrease in the amount of overjet 510.

In some embodiments, tooth repositioning is an unintentional and undesirable side effect of mandibular advancement using intraoral appliances. As discussed herein, the anterior-posterior forces that are applied to the patient's jaws to advance the mandible can be disproportionately distributed onto the anterior teeth, which can be more susceptible to repositioning (e.g., anterior flaring and/or retraction). Accordingly, the intraoral appliances described herein can be designed to eliminate unintentional repositioning of teeth caused by anterior displacement of the mandible. Various approaches can be used to produce such appliances. In some embodiments, the appliance includes a shell having a plurality of teeth-receiving cavities with geometries shaped to reduce or eliminate repositioning of the received teeth of a patient's jaw. For example, the cavities can receive and encapsulate one or more lower anterior teeth in order to reduce or prevent anterior flaring of the lower anterior teeth. As another example, the cavities can receive and encapsulate one or more upper anterior teeth in order to reduce or prevent retraction of the upper anterior teeth. In some embodiments, the appliance can include a pair of interacting appliance shells that receive teeth of the upper and lower jaws, respectively, and include respective cavity geometries designed to reduce or prevent unwanted repositioning of both upper and lower teeth.

In some embodiments, the cavity geometries of an appliance are shaped to match the current arrangement of one or more teeth in order to constrain the teeth to the current arrangement. The cavity geometries can be shaped to maintain all of the teeth in the current arrangement, such that no repositioning is allowed to occur. Alternatively, the cavity geometries can be shaped to maintain some teeth in the current arrangement while allowing for repositioning of other teeth (e.g., in accordance with an orthodontic treatment plan) as described further herein. In such embodiments, the cavity geometries can correspond to a tooth arrangement different from the current tooth arrangement of the patient.

Optionally, the appliance can be manufactured from one or more materials that resist deformation when under load in order to constrain the teeth and prevent repositioning away from the current tooth arrangement. The material(s) can be selected to provide a desired amount of stiffness and/or thickness in order to reduce appliance distortion when worn. For example, the appliance can have an elastic modulus of about 0.5 GPa, 1 GPa, 1.5 GPa, 2 GPa, 2.5 GPa, 2.5 GPa, 3 GPa, or 3.5 GPa. In some embodiments, the appliance has an elastic modulus within a range from about 1 GPa to about 3 GPa. Alternatively or in addition, the appliance can have a thickness of about 5 mils, 10 mils, 15 mils, 20 mils, 25 mils, 30 mils, 35 mils, 40 mils, 45 mils, 50 mils, 55 mils, 60 mils, 65 mils, or 70 mils. In some embodiments, the appliance has a thickness within a range from about 10 mils to about 60 mils. In embodiments where the intraoral appliance is worn only during sleep, there may be more flexibility in the choice of materials compared to other types of intraoral appliances, since factors such as aesthetics (e.g., transparency) may be of less importance. Optionally, appliances that are designed to permit some planned repositioning can have heterogeneous properties, e.g., increased stiffness and/or thickness near teeth that are constrained and reduced stiffness and/or thickness near teeth to be repositioned.

In some embodiments, the intraoral appliances described herein can be designed to apply one or more forces and/or moments to the teeth that reduce or eliminate undesirable tooth repositioning elicited by mandibular advancement. For example, an appliance can be configured to control the distribution of forces applied to the teeth. The amount of mandibular advancement achieved by an appliance depends on the net force (F net) applied to the mandible, the net force being the summation of the forces applied to each tooth. It can be seen that different force distributions can generate the same amount of net force on the jaw. Accordingly, by controlling the force distribution applied to the teeth by the appliance, force loads on teeth susceptible to repositioning can be reduced while achieving the same amount of mandibular advancement.

Figure 6A:
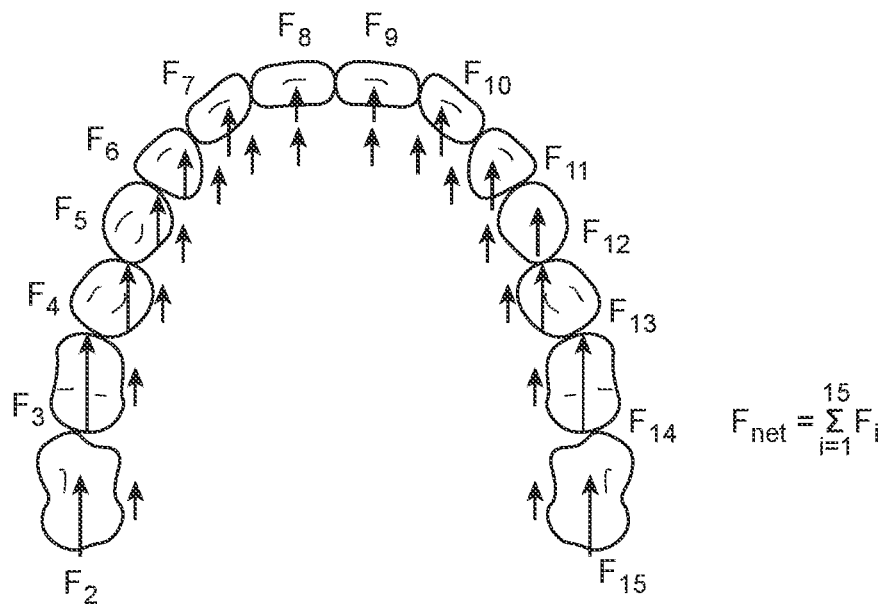
FIGS. 6A and 6B illustrate controlling anterior-posterior force distribution to reduce tooth repositioning elicited by mandibular advancement, in accordance with embodiments.
Figure 6B:
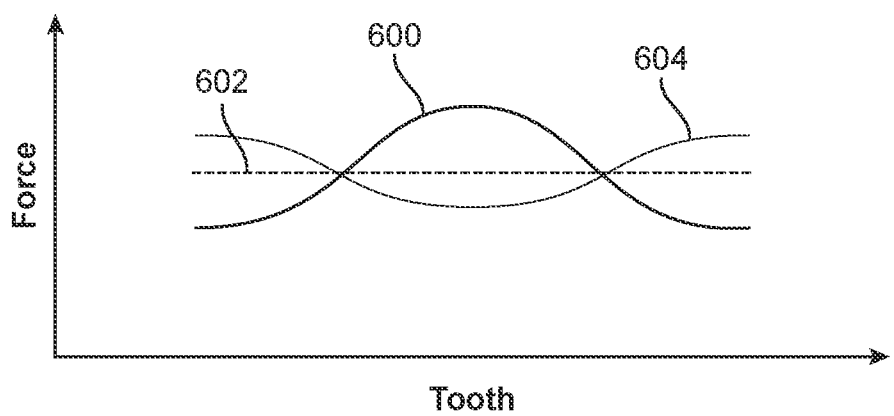

FIGS. 6A and 6B illustrate controlling anterior-posterior force distribution to reduce tooth repositioning elicited by mandibular advancement, in accordance with embodiments. FIG. 6A illustrates the forces applied to individual teeth by different force distributions, while FIG. 6B illustrates the net force profile over the entire arch for different distributions. As discussed herein, a "naive" force distribution 600 applied by an appliance that is not designed to reduce unwanted tooth repositioning can exhibit relatively large forces applied to anterior teeth and relatively small forces applied to posterior teeth. In some embodiments, an intraoral appliance designed to reduce tooth repositioning can produce a uniform force distribution 602 in which each tooth receives an equal amount of force (see inner arrows in FIG. 6A). In other embodiments, an intraoral appliance designed to reduce tooth repositioning can apply a non-uniform or "preferential" force distribution 604 in which certain teeth receive a larger amount of force than other teeth (see outer arrows in FIG. 6A). For example, an appliance shell worn on the lower jaw can exhibit a preferential distribution 604 with larger anterior forces on the posterior teeth and smaller anterior forces on the anterior teeth. Similarly, an appliance shell worn on the lower jaw can exhibit a preferential distribution (not shown) with larger posterior forces on the posterior teeth and smaller posterior forces on the anterior teeth. In the depicted embodiment, the net force applied by each of the three distributions is equal, such that the same amount of mandibular advancement is produced.

Various criteria can be considered in order to determine which teeth should bear larger loads in a non-uniform force distribution. In some embodiments, the determination is performed based on the tooth's resistance to movement, also known as the "anchorage value." Posterior teeth can be more resistant to movement due to their larger root surface area. Additionally, anterior/posterior (mesial/distal) tipping movements of posterior teeth such as molars can be limited due to interference by neighboring teeth, while anterior teeth do not encounter such resistance to buccal/lingual tipping. Accordingly, in some embodiments, it is desirable to preferentially load the posterior teeth in order to minimize unwanted tooth movements.

Alternatively or in combination with the force distribution approaches described herein, an intraoral appliance can be configured to apply one or more forces and/or moments that increase the resistance of one or more teeth to repositioning, referred to herein as "improving anchorage." Various methods can be used to improve anchorage of teeth. For example, the appliance can include cavity geometries shaped to improve anchorage of certain teeth by reducing or inhibiting movement of the teeth along at least one direction of motion, e.g., with respect to up to six degrees of freedom in movement (up to three degrees of freedom in translation and up to three degrees of freedom in rotation) in order to produce improved anchorage. In some embodiments, the anchorage value of a tooth is inversely proportional to the pressure applied to the periodontal ligament (PDL), and certain types of movements produce larger amounts of pressure on the PDL. For example, tipping movements can produce larger loads on the PDL compared to translational movements which load the PDL more uniformly. Accordingly, the anchorage of the tooth can be improved by constraining the tooth to only certain types of movements (e.g., only translational movements) that produce less pressure on the PDL. In some embodiments, this is achieved by applying forces and/or moments to the teeth that oppose the movement to be constrained. Optionally, one or more forces and/or moments can be applied to counteract or oppose a force or moment that would elicit the constrained movement. As another example, anchorage can be improved by constraining multiple teeth to move together, which can increase the resistance to movement due to the increased shared root area.

Figure 7:
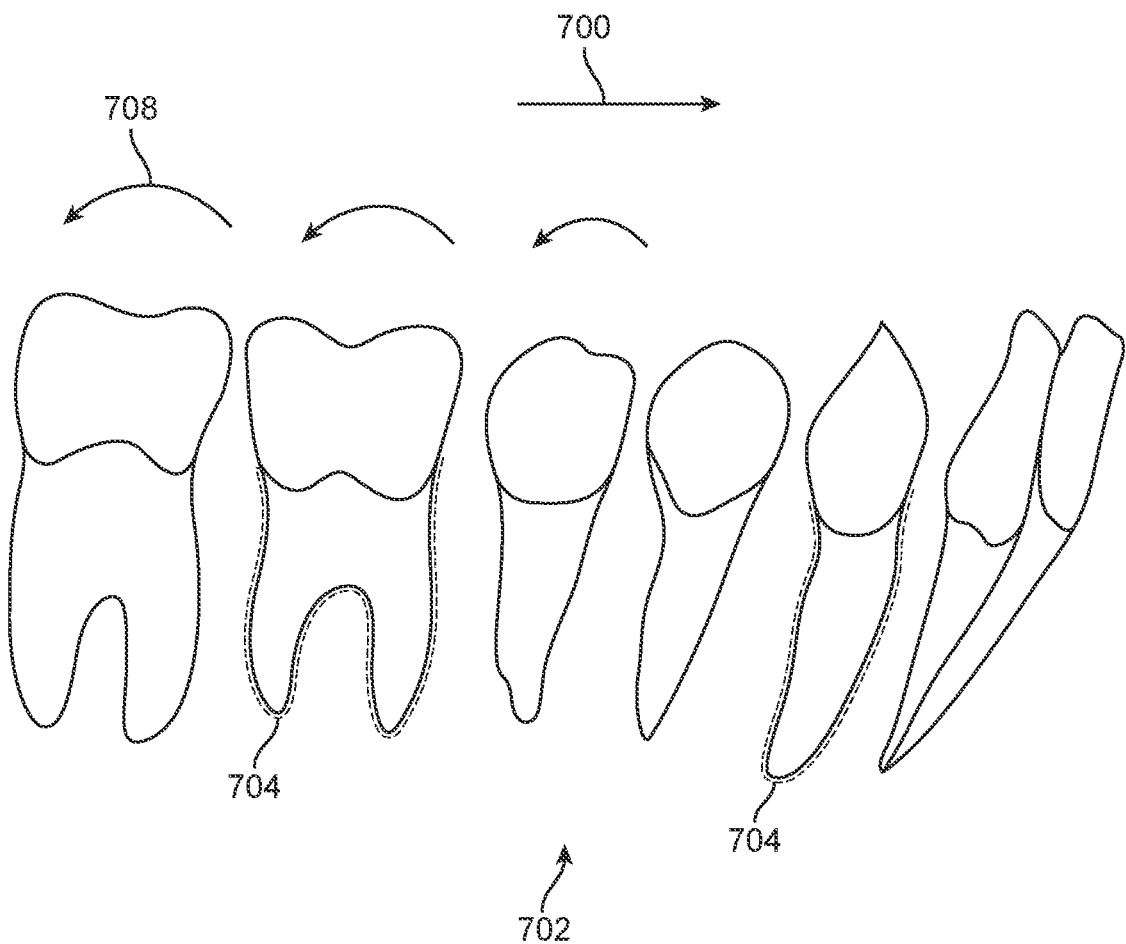
FIG. 7 illustrates improving anchorage to reduce tooth repositioning elicited by mandibular advancement, in accordance with embodiments.

FIG. 7 illustrates improving anchorage to reduce tooth repositioning elicited by mandibular advancement, in accordance with embodiments. A net anterior force 700 is applied to a group of lower teeth 702 to produce anterior displacement of the mandible. Each tooth has a certain amount of root surface area 704 adjacent to the PDL. In order to decrease the amount of pressure exerted on the PDL, the teeth 702 can be constrained to inhibit tipping and permit only translational movements. For example, this can be achieved by designing the appliance to apply one or more moments 708 (e.g., mesial root torques) to the teeth 702 in a direction opposing the force load 700, thereby engaging the teeth 702 while constraining them to a translational movement. The use of opposing moments can additionally be used to compensate and/or counteract undesirable tooth movements, such as anterior flaring. In the embodiment of FIG. 7, each of the moments 708 is applied to an individual tooth. Alternatively or in combination, a single moment can be applied to a group of multiple teeth.

Many different approaches can be used to design intraoral appliances that apply forces and/or moments to teeth to reduce undesirable repositioning (e.g., by controlling the force distribution and/or improving anchorage). In some embodiments, the appliances provided herein include a shell having a plurality of teeth-receiving cavities with geometries shaped to apply a specified system of forces and/or moments, such as a desired force distribution. For example, the cavity geometries can be shaped to exhibit differing amounts of engagement with the received teeth in order to control the resultant forces, moments, and/or force distribution. Engagement can refer to the amount of contact between the inner wall of a tooth-receiving cavity and the exterior surface of the received tooth, for instance. The amount of force applied to a tooth by the appliance can vary based on the extent to which the appliance engages the tooth, e.g., more force is transmitted to more engaged teeth and less force is transmitted to less engaged teeth. Thus, cavities designed to apply relatively large amounts of force to the received teeth can have interior geometries that closely conform to the geometries of the teeth to increase the surface area in contact with the teeth, thus allowing for greater force transmission. In contrast, cavities designed to apply relatively small amount of force or no force to the received teeth can have geometries that differ from the geometries of the received teeth in order to reduce the surface area in contact with the teeth. For instance, a gap or space can be formed between the inner cavity wall and one or more surfaces of the received teeth (e.g., a lingual surface of a lower anterior tooth, a buccal surface of an upper anterior tooth) to reduce or prevent force transmission to the teeth. Accordingly, a desired force distribution (e.g., uniform or non-uniform) can be achieved by shaping the cavity geometries to control the degree of engagement with each tooth. Referring again to the embodiments of FIGS. 6A and 6B, the preferential force distribution 604 can be achieved by increasing engagement of the cavities with the posterior teeth and reducing engagement of the cavities with the anterior teeth. Additionally, in some embodiments, it is beneficial to improve the engagement of the appliance with other portions of the dentition, such as the interproximal regions of teeth, in order to distribute loads across more teeth.

As another example, the forces and/or moments produced by an appliance can be controlled by adjusting the positions and/or orientations of teeth-receiving cavities with respect to up to six degrees of freedom. Differences between the position and orientation of the cavity and the position and orientation of the received tooth can produce forces and/or moments on the tooth, due to elastic deformation of the appliance to accommodate the tooth when the appliance is worn. For example, a cavity that is translated relative to the position of the received tooth can apply a translational force on the tooth along the direction of translation. Similarly, a cavity that is rotated relative to the orientation of the received tooth can apply a moment on the tooth along the direction of rotation. Accordingly, a desired force distribution (e.g., uniform or non-uniform) can be achieved by adjusting the positions and/or orientations of the tooth-receiving cavities relative to the actual tooth arrangement to control the forces and/or moments applied to each tooth. Referring again to the embodiments of FIGS. 6A and 6B, the preferential force distribution 604 can be achieved by positioning the posterior teeth-receiving cavities in a position different from the actual positions of the posterior teeth. For example, the posterior cavities can be positioned in the appliance anteriorly relative to the actual positions of the posterior teeth. Upon placing the appliance on the teeth, the shell would elastically deform and apply an anterior force on the posterior teeth. Similarly, the positions and/or orientations of the tooth-receiving cavities can be adjusted relative to the actual tooth arrangement to apply forces and/or moments that improve anchorage of one or more teeth. Referring again to the embodiment of FIG. 7, the cavity geometries can have an orientation different from the actual orientation of the received teeth in order produce a moment that inhibits tipping.

In some embodiments, modifications to tooth morphology can be used to adjust the forces and/or moments that are applied to the teeth. For example, tooth morphology can be modified by affixing one or more attachments to the surfaces of one or more teeth. Examples of such attachments include buttons, protrusions, brackets, or clips, or any other dental engagement device that is capable of interacting with the appliance to improve engagement, control the applied forces and/or moments, constrain movement of the teeth relative to the appliance, or combinations thereof. In some embodiments, the attachment is manufactured from standard materials for long-term dental use, e.g., materials for dental prostheses or restorations such as composites, so as to allow for long-term treatment without compromising aesthetics. The appliance geometry (e.g., cavity geometries) can be shaped to accommodate the attachment, e.g., via receptacles or apertures that receive the attachment, ridges or dimples that engage the attachment, or combinations thereof. The geometry and placement of such attachments can be designed in order to achieve the desired force and/or moment when the appliance engages the attachments, e.g., in accordance with a specified force distribution and/or to improve anchorage.

In some embodiments, the approaches described herein can be used to produce a plurality of intraoral appliances that are alternatingly worn by the patient in order to produce mandibular advancement while avoiding unintentional repositioning of teeth. Each appliance can produce a different force distribution on the teeth, such that the loading of the teeth is not constant across different appliances. For example, a first appliance can have cavity geometries that apply a first force distribution to the patient's arch, and a second appliance can have cavity geometries that apply a second, different force distribution to the patient's arch. By using different appliances that apply different forces on the teeth, constant loading of the teeth can be avoided, which can reduce or inhibit unintentional tooth movement. Such appliances can be applied to the patient's teeth in various ways. For example, the patient can wear one appliance until unintentional repositioning is observed, then switch to a different appliance in order to alter the force distribution on the teeth. As another example, the patient can alternate between different appliances according to a predetermined schedule (e.g., every other day) in order to vary the forces on the teeth in order to avoid constant loading.

Alternatively or in combination, a patient can be treated with a set of appliances that are alternatingly worn during sleep and when the patient is awake in order to produce mandibular advancement while avoiding unintentional repositioning of teeth. For instance, a first appliance can be worn during sleep in order to reduce sleep apnea and a second appliance can be worn while the patient is awake in order to reverse, reduce, and/or eliminate any unintended movement of the teeth and/or jaws caused by the first appliance. In some embodiments, the second appliance only includes anterior-posterior positioning structures to place the patient's jaws back into the normal occlusion (e.g., structures to retract the mandible relative to the maxilla) and does not include any activations to reposition teeth. In such embodiments, the second appliance would serve primarily as a retainer for maintaining the patient's current tooth arrangement and bite alignment. Alternatively, the second appliance can include activations to reposition one or more teeth (e.g., to correct malocclusion).

The intraoral appliances described herein can be customized for a particular patient. In some embodiments, an appliance is configured to produce a predetermined amount of mandibular advancement that is effective for treating the patient's sleep apnea while reducing the incidence of undesirable side effects such as tooth repositioning, muscle strain, temporamandibular joint (TMJ) dysfunction, bite alterations, and jaw discomfort. For instance, the optimal amount of anterior displacement to be effected by a mandibular advancement treatment plan can be customized according to the patient's jaw anatomy, jaw kinematic data (e.g., jaw border movements, habitual opening amount, maximum opening amount), and/or degree of jaw discomfort experienced. In some embodiments, the practitioner measures characteristics of the patient's jaws in order to determine a suitable amount of mandibular advancement to be applied.

Figure 8:
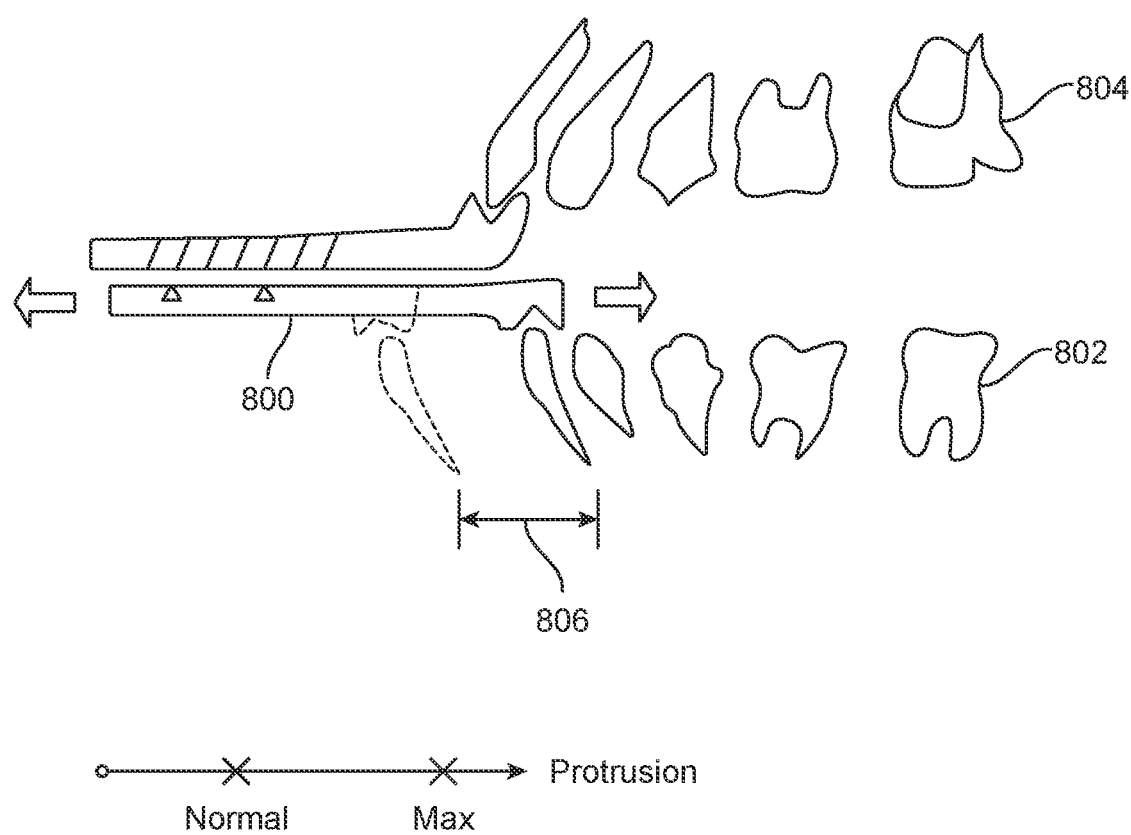
FIG. 8 illustrates a displacement-based approach for determining an amount of mandibular advancement, in accordance with embodiments.

FIG. 8 illustrates a displacement-based approach for determining an amount of mandibular advancement, in accordance with embodiments. In this approach, the practitioner uses a suitable measurement tool (e.g., a protrusion or displacement gauge 800 such as a George Gauge) to obtain measurements of the patient's bite characteristics. For instance, the practitioner can measure the amount of advancement (protrusion) of the patient's lower jaw 802 relative to the upper jaw 804 in the normal bite position, as well as the amount of maximum voluntary protrusion 806 the patient can produce. As with all other types of measurement data described herein, the advancement amount can be measured while the patient is awake and/or during sleep, as desired. In some embodiments, the amount of mandibular advancement to be applied is determined based on these measurements, e.g., as a percentage of the maximum voluntary protrusion such as about 60% of the maximum voluntary protrusion. This approach can be considered to be a "one-dimensional" approach, in that displacement is the only factor considered when determining the degree of jaw advancement.

In some embodiments, purely displacement-based approaches may not be optimal with respect to predicting whether the applied amount of mandibular advancement will cause patient discomfort and other undesirable side effects. Accordingly, certain embodiments presented herein consider other parameters in addition to or instead of displacement, such as an amount of force (e.g., anterior-posterior force) exerted upon the patient's jaws during mandibular advancement. This information can be used to design an appliance customized to exert an amount of force that is appropriate for the particular patient's treatment, e.g., in terms of reducing discomfort, tooth repositioning, etc.

Figure 9:
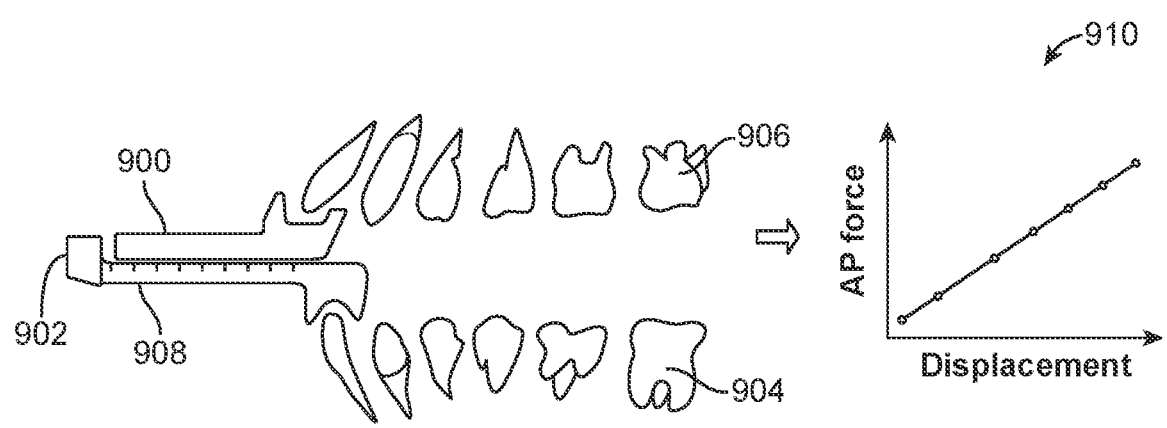
FIG. 9 illustrates a force and displacement-based approach for determining an amount of mandibular advancement, in accordance with embodiments.

FIG. 9 illustrates a force and displacement-based approach for determining an amount of mandibular advancement, in accordance with embodiments. In this approach, the practitioner uses a measurement tool 900 that is capable of measuring the anterior-posterior force applied to the patient's jaws (e.g., via a force sensor or transducer 902) as well as the amount of displacement of the lower jaw 904 relative to the upper jaw 906 (e.g., via an advancement gauge or protrusion gauge 908). In some embodiments, the measurement data is a one-dimensional measurement, e.g., the force and/or displacement are measured along the anterior-posterior direction only. Alternatively, the measurement data can be taken with respect to more than one dimension. For example, a six degree of freedom measurement can be obtained that measures the force along a plurality of different directions in addition to the anterior-posterior direction (e.g., using a six degree of freedom load cell). In some embodiments, other measurement devices besides force sensors are used to obtain force data. For example, electromyography (EMG) measurements of the jaw muscles can be used to measure muscle activity. The EMG data can be input into a biomechanical model of the TMJ system in order to estimate the magnitudes of forces generated. Similarly, jaw displacement can be measured along more than one direction, e.g., using a three degree of freedom gauge that measures displacement along the anterior-posterior, vertical, and/or lateral directions. Alternatively or in combination, six degree of freedom kinematics of the jaws can be determined using other methods, such as ultrasound sensing and/or tracking of reflective markers placed on the jaws.

The measurement data described herein can be taken while the patient is awake and/or asleep, as desired. In some embodiments, the approaches provided herein account for the differences in muscle activity during sleep versus wakefulness. Certain patterns of muscle activation can be unique to sleep, such as rhythmic masticatory muscle activity and/or bruxism. In some embodiments, it may be more physiologically relevant to obtain force and/or displacement measurements while the patient is sleeping. For example, sleep data such as EMG data and/or other polysomnographic (PSG) data can be used as an input for designing the appliances presented herein. The sleep data can be used to directly provide force measurements during sleep, for instance. Alternatively, force measurements can be obtained while the patient is awake, and the sleep data can be used to calibrate the force measurements to account for the differences in physiology during wakefulness versus sleep. Various methods can be implemented in order to calibrate force measurements taken while the patient is awake using the sleep data. In some embodiments, the ratio between the maximum and/or average force values obtained during wakefulness versus sleep can be determined. The ratio can be indicative of the relative muscle activation levels when the patient is awake versus when the patient is asleep, for example. In some embodiments, the muscle activation may be higher during sleep, while in other embodiments, the muscle activation may be higher during wakefulness. Force values obtained while the patient is awake can then be scaled according to the ratio to determine the corresponding force values during sleep. Alternatively or in combination, a biomechanical model of the jaws can utilize sleep data such as EMG data to predict force values during sleep and/or wakefulness in order to calibrate the force measurement data as discussed herein.

Optionally, the force measurement can be combined with other types of data, such as jaw geometry measurements (e.g., obtained by cone beam computed tomography, panographic x-rays, cephalograms, etc.) to predict forces at other locations near the patient's teeth and jaws, such as the TMJ region. Alternatively or in combination, the forces can be predicted from a biomechanical model of the jaws (e.g., with anatomical inputs of the jaws, muscle activation measurement, and/or anatomical statistics), with or without using measurement data from a force sensor. The force data can be used to determine the relationship between the anterior displacement amount and the anterior-posterior force applied to the teeth, e.g., as depicted in the force versus displacement curve 910. The relationship between anterior-posterior force and displacement may be a linear relationship, for example. The force-displacement relationship may vary from patient to patient, e.g., due to patient-specific differences in jaw anatomy, jaw kinematic data, etc. The determined relationship can then be used as a basis for developing patient-specific mandibular advancement appliances. In some embodiments, the measurement data is used to develop a force versus displacement model for the patient that can be used to predict the amount of force associated with a given jaw protrusion input. This approach can be considered to be a "two-dimensional" approach, in that two factors (force and displacement) are considered.

Figure 10:
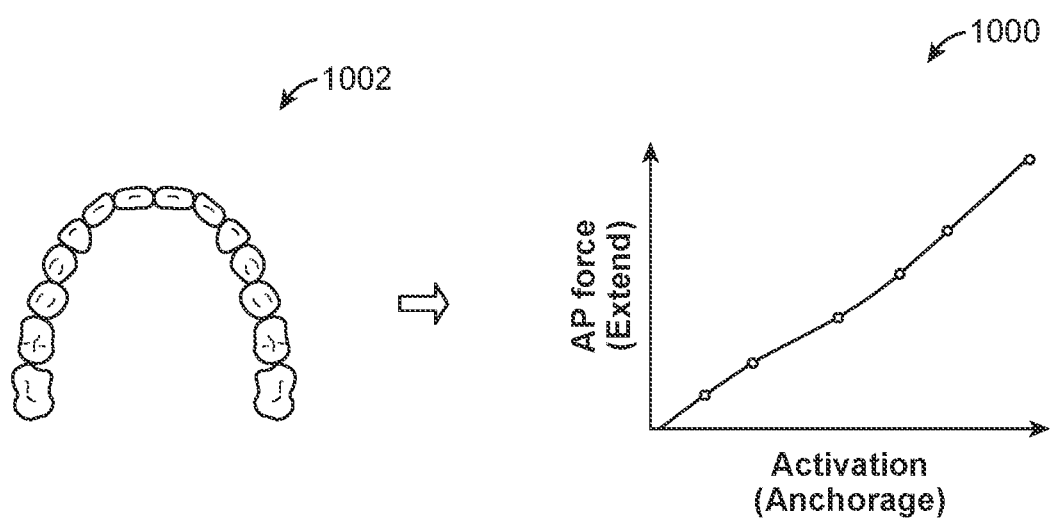
FIG. 10 illustrates a force-based approach for determining an amount of compensation for a mandibular advancement appliance, in accordance with embodiments.

FIG. 10 illustrates a force-based approach for determining an amount of activation for a mandibular advancement appliance, in accordance with embodiments. Activation may be used herein to refer to forces and/or moments to be applied to one or more teeth by the appliance. The patient-specific force measurements described herein can also be used to determine an amount of activation and/or anchorage that is applied to individual teeth in order to reduce unwanted tooth repositioning. The amount of anterior-posterior force applied to a tooth may be linearly related to the amount of activation and/or anchorage that should be applied to the tooth to prevent repositioning, e.g., as depicted in the force versus activation/anchorage curve 1000. This relationship information can be used as a basis for intraoral appliance design.

In some embodiments, a laboratory model of the teeth 1002 can be used to determine the relationship between anterior-posterior force and activation and/or anchorage. In some embodiments, the laboratory model is used to predict force distributions that can inform the force and/or moment activations to be applied to the teeth. The laboratory model can provide a black box transfer function with jaw displacement and the associated anterior-posterior forces (e.g., forces measured in vivo) as inputs, and the resultant force distribution on the teeth as an output. Various types of laboratory models are suitable for use with the embodiments presented herein. For example, the laboratory model can include physical tooth models coupled to load cells. As another example, the laboratory model can be a computer simulation with virtual tooth models.

Figure 11:
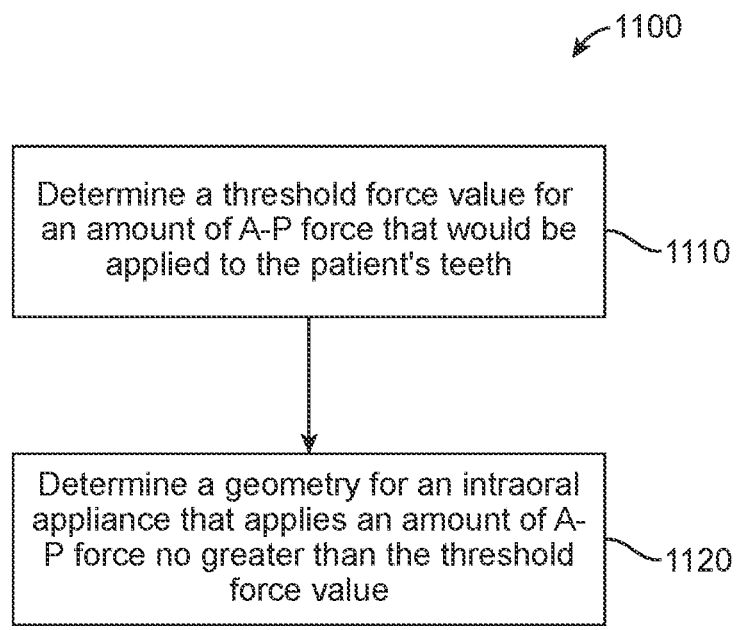
FIG. 11 illustrates a method for producing an intraoral appliance for treating sleep apnea in a patient, in accordance with embodiments.

FIG. 11 illustrates a method 1100 for producing an intraoral appliance for treating sleep apnea in a patient, in accordance with embodiments. One or more steps of the method 1100 can be performed by one or more processors, e.g., one or more processors of a computer system configured for designing appliances. Alternatively or in combination, one or more steps can be performed by a treating professional such as an orthodontic practitioner. The method 1100 can be used to produce any of the appliances described herein.

In step 1110, a threshold force value is determined for an amount of anterior-posterior (A-P) force that would be applied to the patient's teeth in order to displace the patient's lower jaw anteriorly relative to the upper jaw. The threshold force value can be no greater than amount of anterior-posterior force that is associated with side effects such as patient discomfort, undesirable tooth repositioning, and/or TMJ dysfunction. For example, the threshold value can be about 1 N, 2 N, 5 N, 10 N, 15 N, 20 N, or 25 N, or within a range from about 0.5 N to about 20 N. The threshold value can be a standardized value that is applied to most or all patients. Alternatively, the threshold value can be customized for each particular patient, e.g., based on the force-displacement measurements described herein.

In step 1120, a geometry for an intraoral appliance is determined based on the threshold force value, such that the appliance is configured to apply an amount of anterior-posterior force to the patient's teeth that is no greater than the threshold force value. In some embodiments, the intraoral appliance is configured to displace the lower jaw anteriorly relative to the upper jaw when worn by the patient in order to treat the sleep apnea. For instance, the appliance can include an upper shell with an upper advancement structure and cavities for receiving the upper teeth, and a lower shell with a lower advancement structure with cavities for receiving the lower teeth, with the upper and lower advancement structures being arranged to engage each other to produce mandibular advancement, as discussed herein. Optionally, the appliance can have cavity geometries shaped to reduce undesirable tooth repositioning elicited by the advancement, as described herein.

The geometry of the appliance (e.g., the geometry of the tooth-receiving cavities and/or advancement structure(s)) can be determined in various ways. In some embodiments, the geometry can be determined based on received measurement data indicative of a patient-specific relationship between the anterior displacement amount and the amount of anterior-posterior force applied to the teeth, as described herein. This relationship can be used to determine a threshold displacement value corresponding to the threshold force value, and the appliance can be configured to advance the lower jaw by an amount no greater than the threshold displacement value.

In alternative embodiments, rather than using a threshold force value that serves as an upper limit on the amount of force to be applied to the teeth, a target force value can be determined for an amount of anterior-posterior (A-P) force that would be applied to the patient's teeth in order to displace the patient's lower jaw anteriorly relative to the upper jaw. The target force value can be an amount of anterior-posterior force that does not produce side effects such as patient discomfort, undesirable tooth repositioning, and/or TMJ dysfunction. For example, the target force value can be about 1 N, 2 N, 5 N, 10 N, 15 N, 20 N, or 25 N, or within a range from about 0.5 N to about 20 N. Accordingly, the appliance geometry (e.g., cavity geometries) can be determined based on the target force value, such that the appliance is configured to apply an amount of anterior-posterior force to the patient's teeth that substantially matches the target force value (e.g., is within 20%, 10%, 5%, 1%, 0.5%, 0.1%, or 0.01% of the target force value). Optionally, a target displacement value corresponding to the target force value can be determined, and the appliance can be configured to advance the lower jaw by an amount substantially matching the target displacement value (e.g., is within 20%, 10%, 5%, 1%, 0.5%, 0.1%, or 0.01% of the target displacement value).

Alternatively or in combination, a method for producing an intraoral appliance for treating sleep apnea can involve determining the forces (e.g., anterior-posterior forces) applied to the upper and/or lower jaws at a targeted or optimal displacement amount for treating sleep apnea. The displacement amount can be based on patient-specific factors such as anatomy, jaw kinematics, sleep apnea severity, patient comfort, and the like. The forces used to produce the displacement amount can be determined in various ways, e.g., by in vivo measurements and/or the modeling approaches described herein. Subsequently, the mandibular advancement appliance can be designed using these forces as an input.

In some embodiments, the appliance design methods described herein also account for other forces applied on the patient's teeth besides anterior-posterior forces. For example, a suboptimal vertical or occlusal force distribution can also influence the incidence of side effects such as jaw stability, TMJ dysfunction, and unintentional tooth repositioning. Accordingly, appliances herein can be designed to improve the distribution of occlusal forces on the teeth, e.g., by distributing occlusal forces across a larger number of teeth, reducing occlusal forces on anterior teeth, increasing occlusal forces on posterior teeth, or combinations thereof. For example, the appliance can include occlusal structures situated at various points along the arch in order to create additional occlusal contact points that facilitate distribution of occlusal forces. As another example, in some embodiments, inappropriate occlusal contacts between teeth (e.g., anterior occlusal contacts) can create instability, and occlusal structures can be used to shift the occlusal load to a more appropriate region of the dental arch (e.g., the posterior teeth) in order to improve stability.

In some embodiments, occlusal structures (e.g., platforms, ramps, protrusions, etc.) are placed on the appliance to create contact points independent of the anterior-posterior axis. For example, the occlusal structures can be parallel or substantially parallel to the occlusal plane to create controlled contact points normal to the occlusal plane. This can be used to strategically distribute occlusal loads or to position the mandible in the vertical dimension (e.g., to control the amount of mouth opening). The occlusal structures can be ramped at an angle offset from the occlusal plane to provide a lateral component to the contact. Such occlusal structures can be positioned and angled to recreate or mimic aspects of normal healthy occlusion, such as canine guidance. In some embodiments, the occlusal structures can mimic the natural intercuspation of the teeth, e.g., by incorporating surface geometries that mimic the geometries of the cusps on the teeth (e.g., molar cusp geometries). The intercuspated surface geometries can be offset relative to the patient's actual tooth geometry in order to accommodate the protruded mandibular position. The use of such intercuspated surface geometries can facilitate application of occlusal loads at the desired locations (e.g., on the posterior teeth).

Figure 23A:
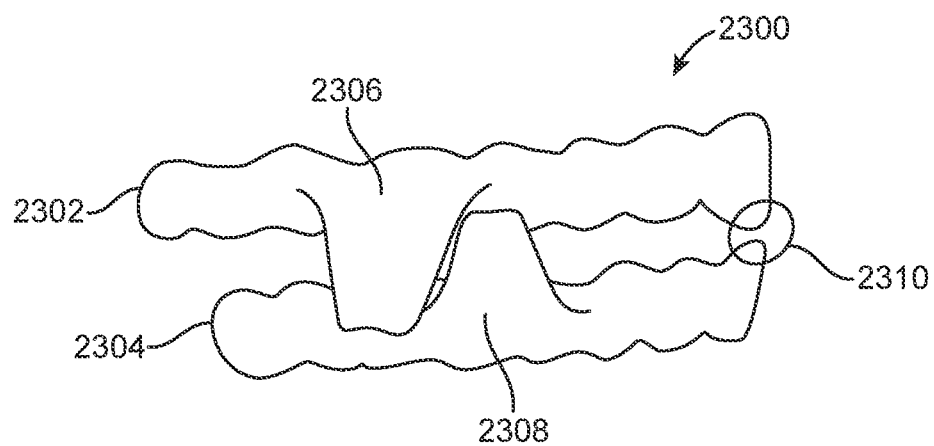
FIGS. 23A through 23C illustrate optimizing occlusal force distribution on the teeth, in accordance with embodiments.
Figure 23B:
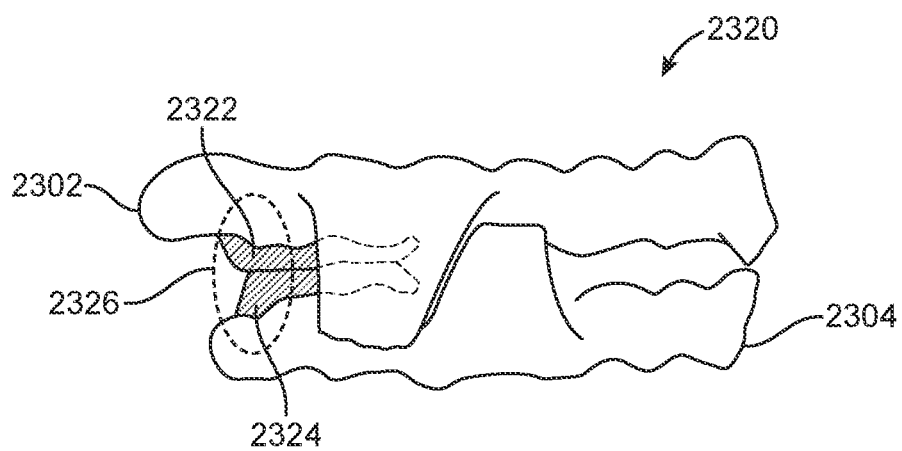
Figure 23C:
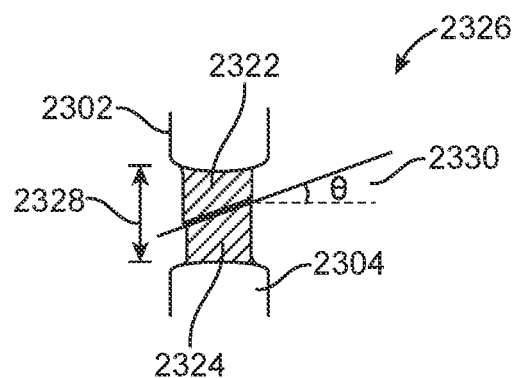

FIGS. 23A through 23C illustrate optimizing occlusal force distribution on the teeth, in accordance with embodiments. In the appliance 2300, the upper shell 2302 and lower shell 2304 produce mandibular advancement via the engagement of upper and lower advancement structures 2306, 2308. In some embodiments, when the mandible is in the advanced position, the occlusal contact points between the upper and lower teeth are primarily located on the anterior teeth, thus producing a region of relatively high occlusal pressure 2310. This can create an unequal occlusal force (force along the vertical axis) that can result in problems with respect to jaw stability, TMJ dysfunction, and unwanted tooth movements.

FIG. 23B illustrates a modified appliance 2320 in which posterior occlusal structures 2322, 2324 have been added to the upper and lower shells 2302, 2304, respectively in order to create additional posterior occlusal contact points to distribute the occlusal forces onto the posterior teeth and away from the anterior teeth. The appliance 2320 can include two pairs of such occlusal structures, e.g., one on the left side and one on the right side. FIG. 23C illustrates a posterior view of the region 2326 of the appliance 2320 (indicated by the dashed circle in FIG. 23B). The various characteristics of the posterior occlusal structures 2322, 2324 can be varied as desired in order to create a desired amount of vertical space between the jaws, reduce lateral jaw movements, and/or create three-dimensional movements in order to reflect the actual movement of the jaw when extended during sleep. For example, the height 2328 of the occlusal structures 2322, 2324 can be increased or decreased as desired to accommodate the natural occlusal separation between the jaws during sleep (e.g., if the patient is an open breather who sleeps with the mouth open). In embodiments where two pairs of occlusal structures are used (e.g., a left pair and a right pair), the heights of the two pairs can be the same (e.g., to provide symmetry) or different (e.g., to control rotation of the mandible about the anterior-posterior axis). As another example, the angle 2330 of the interface between the occlusal structures 2322, 2324 can be varied in order to control the extent of permitted lateral movements of the jaws relative to each other. In some embodiments, a larger angle inhibits lateral movements while a smaller angle permits lateral movements. Optionally, the angle 2330 can be used to control the amount of vertical opening dependence on lateral motion, similar to canine guidance during lateral jaw motions. In such embodiments, the occlusal structures 2322, 2324 can be used to preferentially distribute lateral loads on the canines in order to avoid unwanted lateral loading of the molars during lateral mandibular movements, e.g., by positioning the occlusal structures over the canines. In some embodiments, angulated occlusal structures are used to control and/or guide the lateral motions of the jaws while permitting jaw opening and/or jaw closing motions. Constraint of lateral jaw movements can increase the stability with which the jaws are maintained in the specified position, thus reducing the likelihood of the upper and lower shells 2302, 2304 becoming inadvertently disengaged from each other during sleep due to lateral motion.

In some embodiments, the appliance design approaches presented herein involve modifying one or more parameters of an advancement structure in order to produce a desired amount of mandibular displacement and/or displacement force. As discussed herein, an appliance can include an advancement structure that engages with an opposing jaw (e.g., directly, or indirectly via a second advancement structure) to produce the protrusive force that advances the lower jaw. The shape and/or position of the advancement structure can determine the extent to which the jaw is displaced and the stability with which the jaw is maintained in the advanced position. Additionally, the configuration of the advancement structure can influence patient comfort, as larger amounts of jaw displacement and/or constraint of jaw movement can increase discomfort. Accordingly, the placement, positioning, and/or geometry (e.g., size, shape) of mandibular advancement structures on the shells of intraoral appliances can be optimized, e.g., in order to maximize mandibular advancement distance, mandibular advancement stability, and/or patient comfort.

Various methods can be used to produce the optimized appliances described herein. In some embodiments, an appliance can be produced with customized advancement structures having a specified position and/or geometry to produce a desired jaw configuration. In other embodiments, the mandibular advancement appliances described herein can be fabricated with generic advancement structures that can be subsequently adjusted by the treating professional to the desired position and/or geometry in order to produce the desired jaw configuration. For instance, an adjustable appliance can include an advancement structure with one or more movable portions that can be moved relative to the appliance in order to modify the position and/or geometry of the advancement structure. As another example, an adjustable appliance can include an advancement structure with one or more removable portions that can be added or removed from the appliance to produce a desired geometry. In such embodiments, the structure can include markings to indicate the portion(s) that should be added or removed to produce a certain amount of displacement. For example, an appliance can include a mandibular advancement structure having removable portions that can be used to alter the thickness and/or shape of the structure in order to achieve a desired amount of movement for a given treatment stage. The structure can include markings indicating how much of the structure should be removed to achieve a desired amount of jaw advancement. In some embodiment, the treating professional is provided with a plurality of adjustable appliances and makes different adjustments to each one in order to create a series of appliances that produce differing degrees of mandibular advancement.

Figure 12:
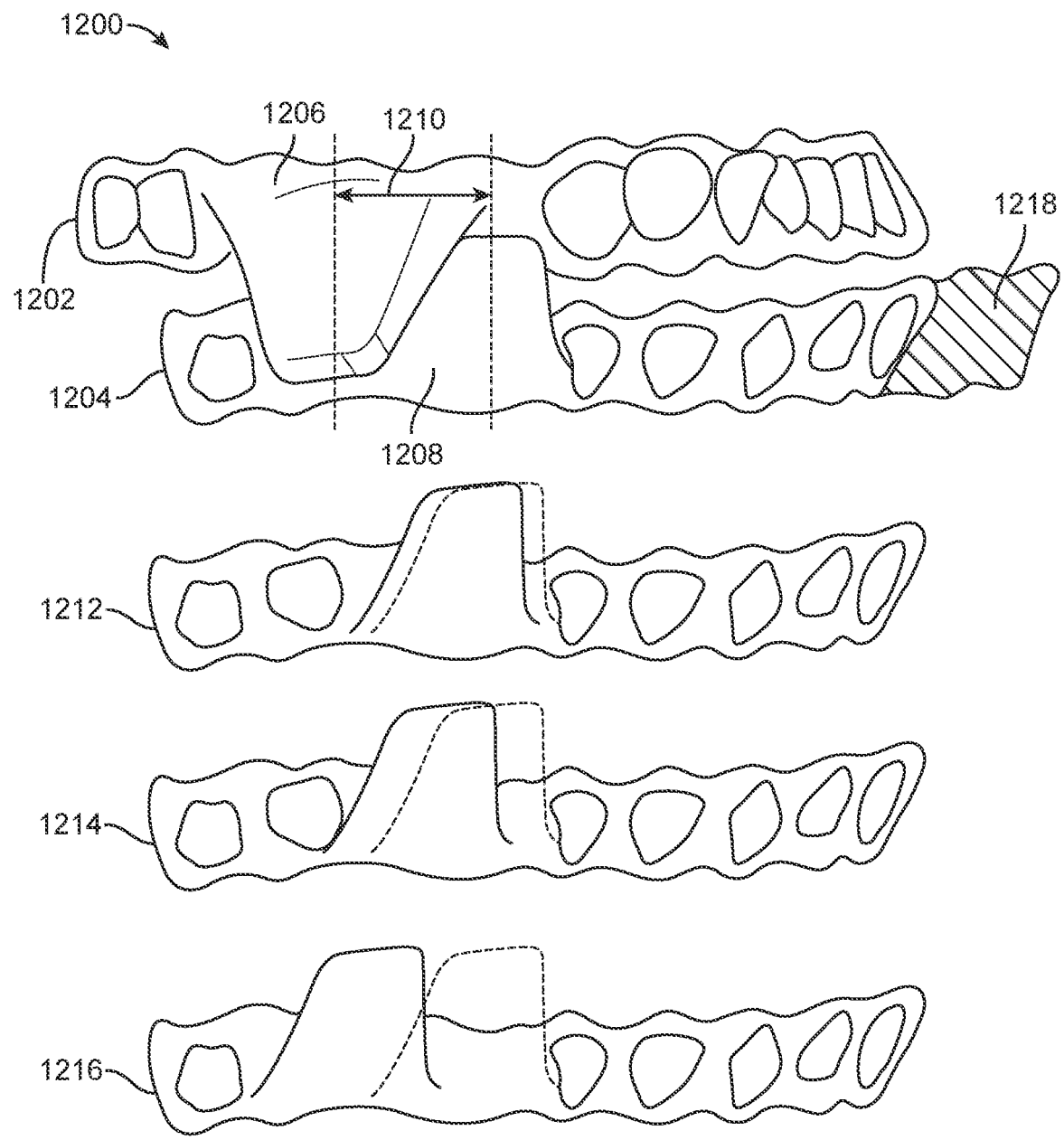
FIG. 12 illustrates optimizing the position of an advancement structure, in accordance with embodiments.
Figure 13A:
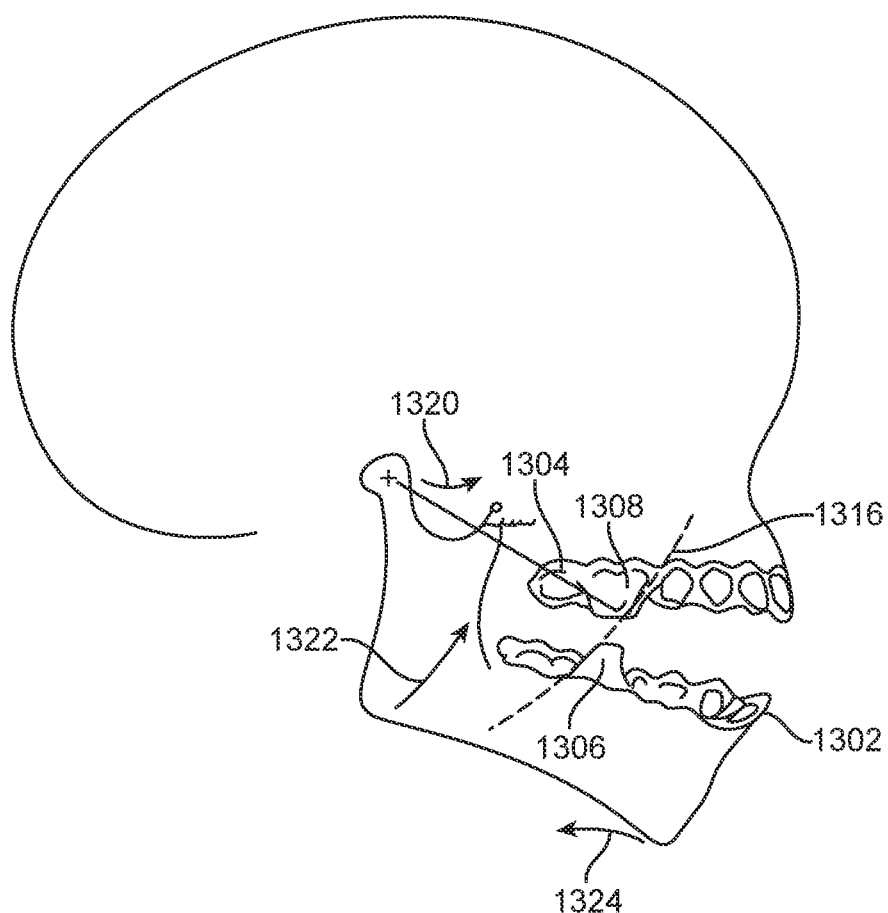
FIGS. 13A through 13D illustrate optimizing the geometry of an advancement structure, in accordance with embodiments.
Figure 13B:
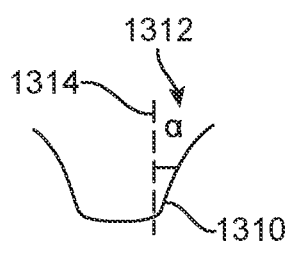
Figure 13C:
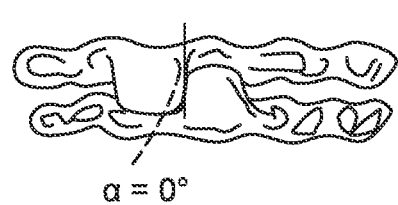
Figure 13D:
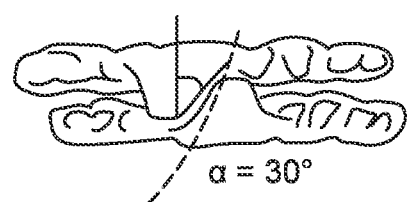

FIG. 12 illustrates optimizing the position of an advancement structure, in accordance with embodiments. In the depiction of FIG. 12, the mandibular advancement appliance 1200 comprises an upper shell 1202 and lower shell 1204 with respective protruding advancement structures 1206, 1208, similar to the embodiment of FIG. 2. The advancement structures 1206, 1208 engage with each other when the shells 1202, 1204 are brought together (e.g., when the patient's jaws are closed) to advance the mandible anteriorly. As shown in FIG. 12, the degree of mandibular advancement can be be controlled by relative positioning of the advancement structures 1206, 1208 along the upper and lower shells 1202, 1204 and/or the centerline-to-centerline distance 1210 between the advancement structures 1206, 1208. In some embodiments, the degree of mandibular advancement can be determined by the positioning of the upper and lower mandibular advancement structures 1206, 1208 on their respective arches. For a given relative jaw position, the lower jaw mandibular advancement structure 1208 can be placed more posteriorly in order to increase the mandibular advancement. Accordingly, the positioning of the upper advancement structure 1206 and/or the lower advancement structure 1208 can be varied in order to achieve a desired amount of jaw displacement. For example, in the depiction of FIG. 12, the lower shells 1204, 1212, 1214, 1216 each have a respective advancement structure that is located at a different position along the anterior-posterior axis of the appliance. Each lower shell 1204, 1212, 1214, 1216 can produce a different amount of mandibular advancement when worn with the upper shell 1202. The shells 1204, 1212, 1214, and 1216 can be configured to produce increasing amounts of advancement up to a maximum or targeted advancement amount 1218.

In some embodiments, a mandibular advancement system is provided that includes a primary appliance (e.g., a shell appliance worn on one jaw) and a plurality of secondary appliances (e.g., shell appliances worn on the opposing jaw) useful for selectively achieving different degrees of mandibular advancement. Each secondary appliance can produce a different amount of jaw advancement when engaged with the primary appliance. Accordingly, different secondary appliances can be sequentially applied to the patient, for example, to titrate for an optimal or targeted amount of mandibular advancement, or to produce incremental staging towards a targeted or optimal advanced position to mitigate patient discomfort. In some embodiments, the patient can select which of the secondary appliances is preferred for treatment.

For example, during the diagnostic stage, an optimal or targeted mandibular advancement amount can be determined for the patient. A system of oral appliances can be fabricated and delivered to the doctor, e.g., using the scanning and fabrication procedures as are well known in the art as described further herein. Alternatively or in combination, a plurality of upper shells configured to be worn with a lower shell can be fabricated. This allows for the production of a set of intraoral appliances including a single upper or lower appliance shell with a plurality of mating appliance shells, where the advancement structure on the mating shell is slightly offset from the structure on the other shells, e.g., by a distance in the range from about 0.1 mm to about 1 mm. The patient can then wear the shell with the fixed advancement structure and choose from the plurality of mating shells to achieve a desired degree of mandibular advancement. To make an adjustment to the mandibular advancement dosage, only one of the shells (e.g., the lower shell) need be replaced. The treatment can thus be adjusted by the patient between visits to the physician and/or fabrication of new appliances.

Alternatively or in combination with the position-based customization described herein, the geometric parameters of the advancement structure can also be modified, e.g., based on patient-specific factors and/or the desired treatment regimen. Examples of such geometric parameters include but are not limited to structure height, width, thickness, angle, and shape. By adjusting the geometry of the advancement structure, appliances can be designed in a patient-specific manner to produce a specified jaw configuration (e.g., amount of mandibular advancement, amount of vertical distance between upper and lower jaws, etc.).

FIGS. 13A through 13D illustrate optimizing the geometry of an advancement structure, in accordance with embodiments. Similar to the embodiment of FIG. 12, the mandibular advancement appliance includes a lower shell 1302 and upper shell 1304 with respective protruding advancement structures 1306, 1308. The advancement structures 1306, 1308 include respective engagement surfaces shaped to engage with each other in order to urge the lower jaw anteriorly. In some embodiments, the engagement surface 1310 is characterized by an inclination angle 1312 that indicates the extent to which the surface 1310 is rotated from the vertical axis 1314. For example, an inclination angle of 0° (see, e.g., FIG. 13C) can indicate that the engagement surface is parallel to the vertical axis and perpendicular to the anterior-posterior axis, whereas an inclination angle of 30° (see, e.g., FIG. 13D) can indicate that the engagement surface is at an angle relative to the vertical axis. Paired advancement structures can have engagement surfaces with the same inclination angle in order to facilitate mating of the engagement surfaces.

In some embodiments, the inclination angle influences various treatment parameters such as the mandibular advancement amount, advancement stability, and degree of discomfort experienced by the patient. For instance, a larger inclination angle can produce a larger amount of mandibular displacement while a smaller inclination angle can produce a smaller amount of displacement. As another example, advancement structures with a larger inclination angle can be more prone to becoming disengaged and therefore can be less stable than structures with smaller inclination angles. In yet another example, a larger inclination angle can be associated with increased patient comfort, e.g., due to reduced resistance to certain jaw movements such as jaw opening movements, while a smaller inclination angle can be associated with decreased patient comfort, e.g., due to increased jaw opening resistance. The correlations between inclination angle and treatment parameters can vary based on the specific anatomy and kinematics of the patient's jaw. Accordingly, the inclination angle for an engagement surface can be determined based on any suitable combination of the patient's jaw anatomy, jaw kinematic data, targeted displacement distance, or targeted amount of patient comfort. In some embodiments, the inclination angle can be based on the specific anatomy of the muscles in and around the jaw, such as the external pterygoid muscle 1320, masseter muscle 1322, and/or geniohyoid, mylohyoid, and digastric muscles 1324 (arrows indicate directionality of the muscles).

Optionally, the inclination angle can be designed based on the patient's habitual jaw opening trajectory 1316. An appliance with an inclination angle that more closely corresponds to the angle of the trajectory (see, e.g., FIG. 13D) can be more comfortable to wear than one that has an angle different from the trajectory (see, e.g., FIG. 13C), due to reduced resistance of the advancement structures to jaw opening and closing movements. However, such appliances can be more susceptible to becoming inadvertently disengaged.

Figure 14:
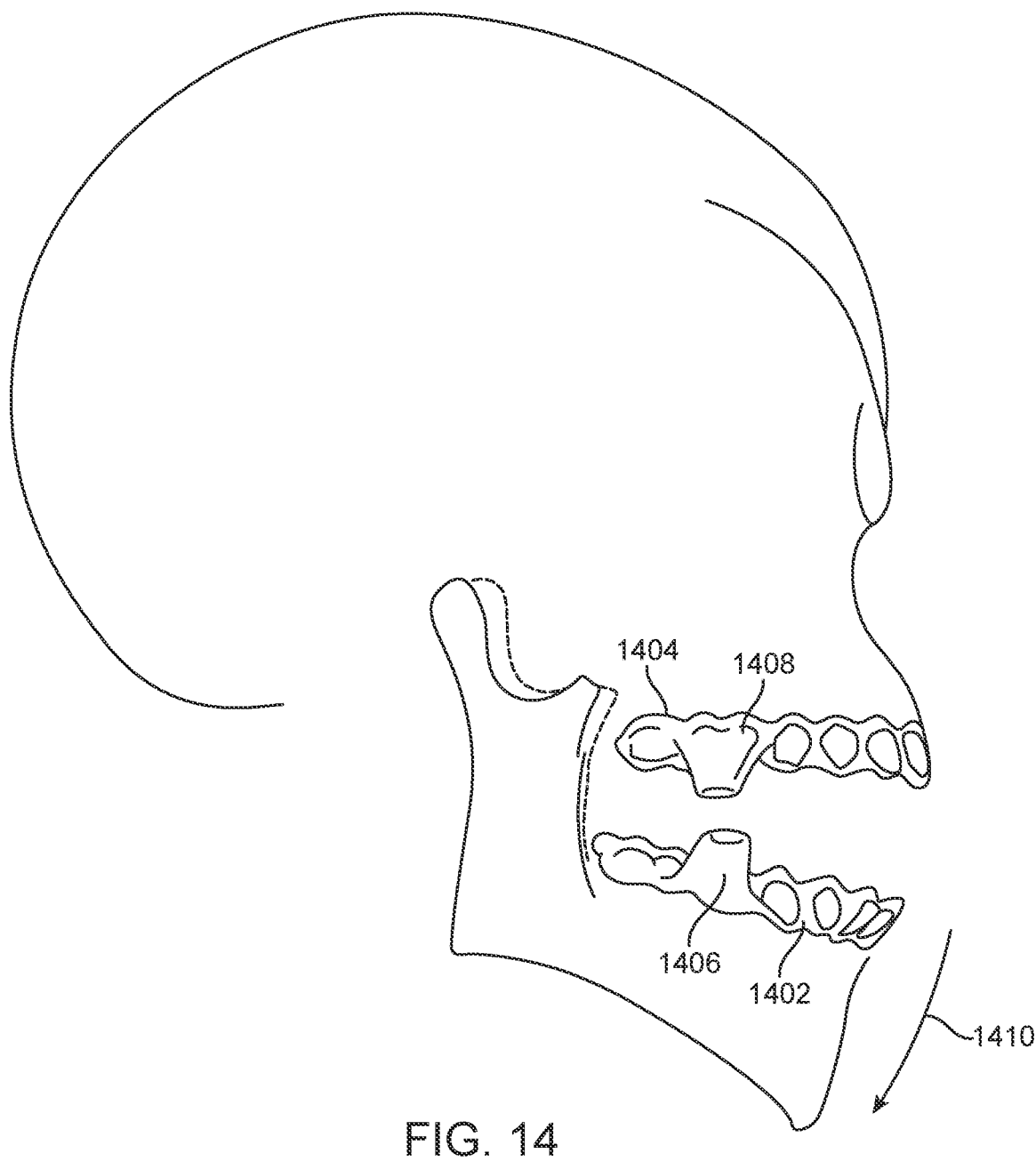
FIG. 14 illustrates loss of mandibular advancement due to disengagement of advancement structures, in accordance with embodiments.

FIG. 14 illustrates loss of mandibular advancement due to disengagement of advancement structures, in accordance with embodiments. The mandibular advancement device of FIG. 14 includes a lower shell 1402 and upper shell 1404 with respective protruding advancement structures 1406, 1408 configured to engage each other, similar to other embodiments described herein. In some embodiments, the advancement structures 1406, 1408 become disengaged during use, e.g., due to passive mouth opening of the patient (see, e.g., arrow 1410). For example, during sleep, the jaw may tend to open for some patients. Disengagement of the structures 1406, 1408 can result in the reversion of the mandible to the habitual configuration, thus compromising the effectiveness of the sleep apnea treatment.

Accordingly, various embodiments of the intraoral appliances provided herein include a coupling mechanism to prevent inadvertent disengagement of advancement structures, as well as to bias the advancement structures toward a targeted arrangement in order to maintain a desired jaw configuration (e.g., with respect to amount of mandibular advancement, jaw opening distance, etc.). In some embodiments, the coupling mechanism includes a first coupling element of an upper advancement structure of an upper appliance shell, and a second coupling element of a lower advancement structure of a lower appliance shell. The coupling elements can include, for example, magnetic elements, elastic tethers, mating features, adhesive components, or combinations thereof. The first and second coupling elements can interact with each other to maintain the upper and advancement structures in engagement with each other. Alternatively or in combination, the coupling elements can be arranged to bias the advancement structures toward predetermined relative positions, e.g., to produce an optimal jaw configuration for treating sleep apnea while mitigating discomfort. In some embodiments, this biasing is reversible, such that the patient is able to disengage the structures if sufficiently large movements and/or forces are applied (e.g., in order to remove the appliance). The use of reversible biasing elements can improve comfort and ease of use of the appliance by allowing for voluntary separation of the patient's jaws, while providing resistance to involuntary disengagement during treatment.

In some embodiments, to promote engagement of advancement structures, magnets can be embedded into the advancement structures as shown in various embodiments herein. The number, strength, and position/orientation of magnets on the advancement structures may all be selected to provide particular treatments for individual patients. In some embodiments, in contrast to other uses of magnets in mandibular advancement devices, the embodiments herein do not use magnetism to effect advancement, but rather use magnetism to properly position the upper and lower appliance shells as well as to promote closed-mouth sleeping, which can be desirable for device effectiveness and for healthy oral hygiene. In some embodiments, the magnets not only allow the advancement structures to prevent mandibular retrusion (retraction), but can also be positioned to allow or eliminate any vertical gap between the upper and lower shells, allowing an additional treatment variable for particular patients. The use of magnetic elements in the appliances described herein is particularly advantageous in some embodiments since they are able to stabilize the jaws at a desired position while allowing the jaws to periodically open, close, and comfortably return to the correct positions. Additionally, the strength of the magnetic elements can be varied to achieve a desired degree of stabilization, with stronger magnets promoting retention.

Figure 15A:
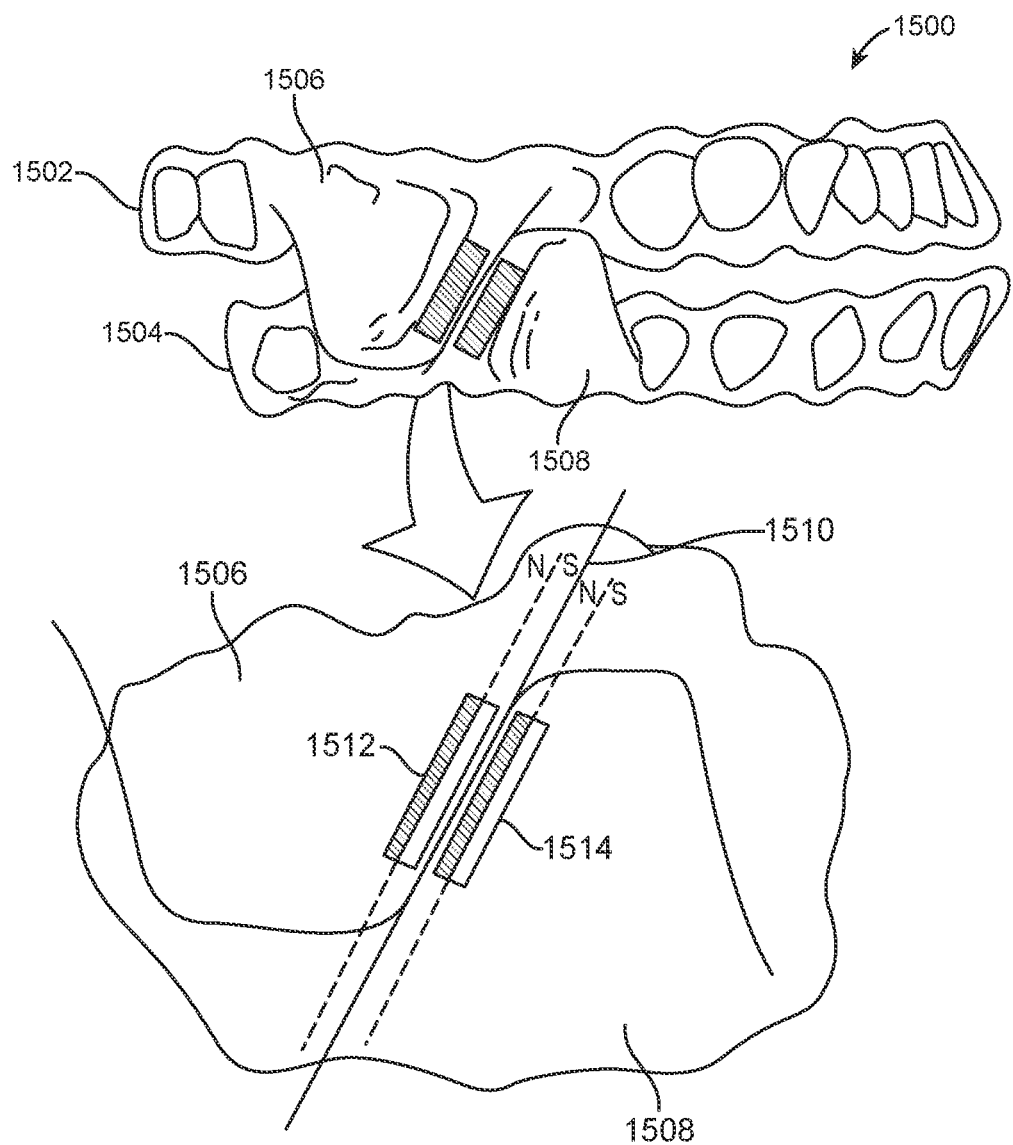
FIGS. 15A through 15C illustrates a magnetic coupling for advancement structures, in accordance with embodiments.
Figure 15B:
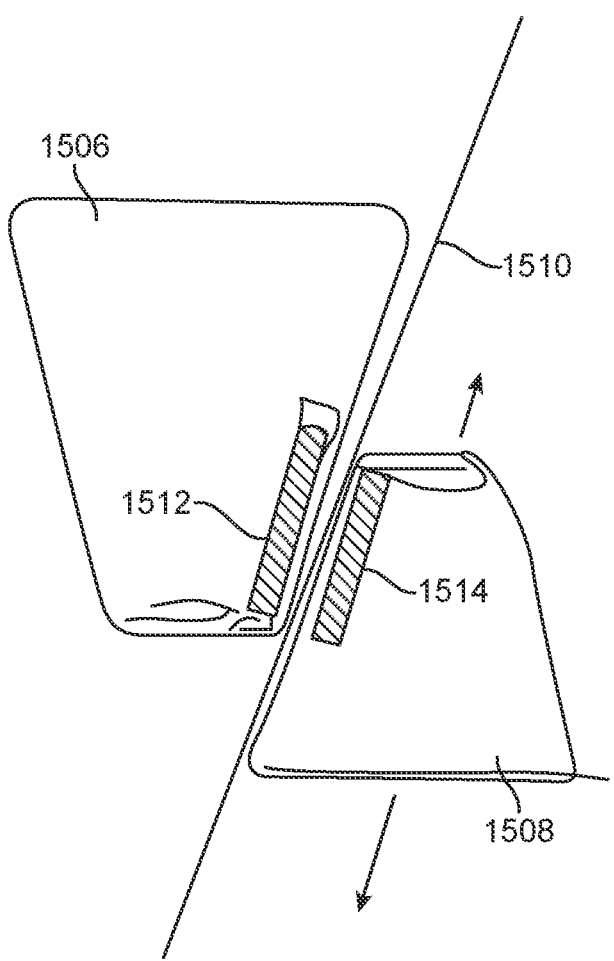
Figure 15C:
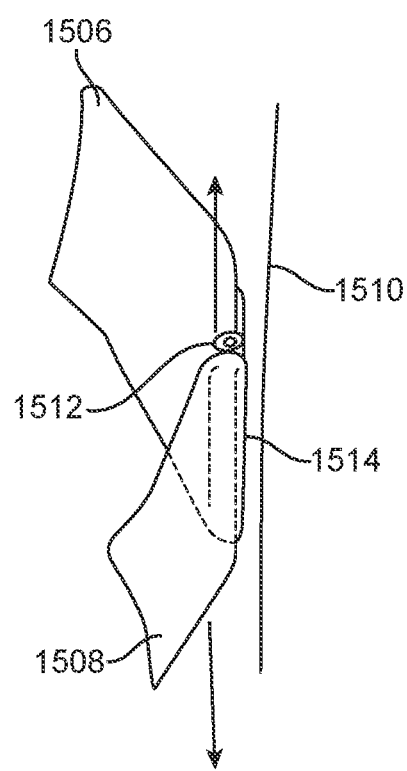

FIG. 15A illustrates a magnetic coupling for advancement structures, in accordance with embodiments. FIGS. 15B and 15C illustrates sagittal and frontal views of the magnetic coupling of FIG. 15A, respectively. The appliance 1500 includes upper and lower shells 1502, 1504 that engage each other via respective advancement structures 1506, 1508 to advance the mandible. In some embodiments, the structures 1506, 1508 have mating anterior and posterior surfaces, respectively, that mate along an engagement plane 1510 to effect the advancement. The inclination angle of the engagement plane 1510 relative to the vertical axis can be varied according to patient-specific factors and the prescribed treatment plan, as discussed herein. The upper structure 1506 can include an upper magnetic element 1512 and the lower structure 1508 can include a lower magnetic element 1514. The magnetic elements 1512, 1514 can be positioned near the engagement plane 1510 and arranged such that the attractive magnetic forces reversibly bias the structures 1506, 1508 towards the engaged configuration. By comparing FIGS. 15A through 15C, it can be seen that by adjusting (1) the angle of the engagement plane 1510 relative to a transverse plane passing between the jaws and (2) the positions of the magnetic elements 1512, 1514 along the engagement plane 1510 (e.g., in a generally upward or downward direction), the amount or distance of the mandibular advancement can be controlled as well, as the magnitude of the gap between the upper and lower shells 1502, 1504.

Figure 16A:
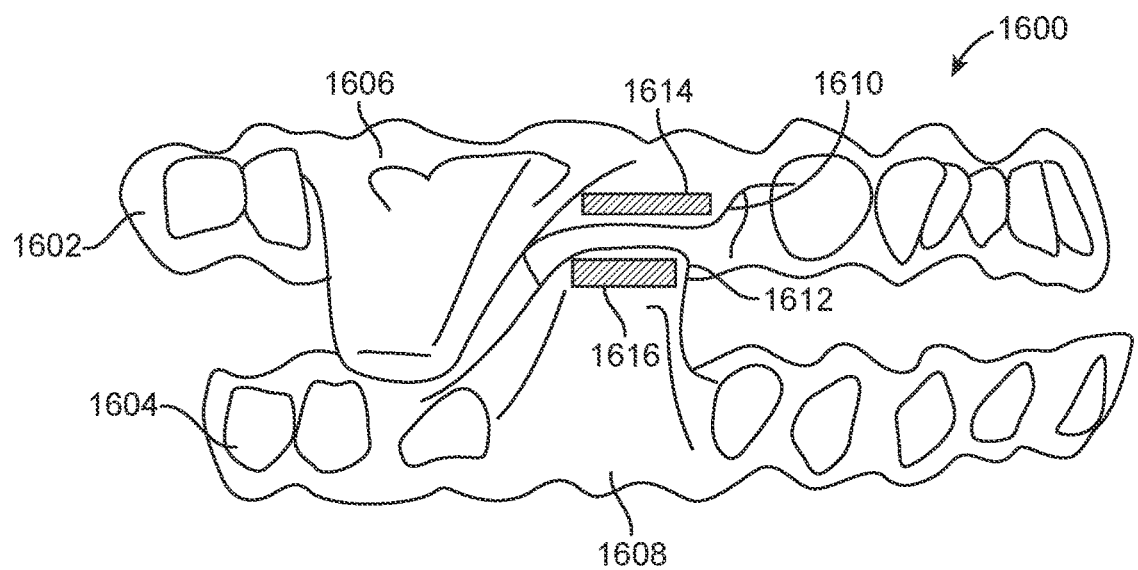
FIG. 16A illustrates an alternative magnetic coupling for advancement structures, in accordance with embodiments.

FIG. 16A illustrates an alternative magnetic coupling for advancement features, in accordance with embodiments. The appliance 1600 includes upper and lower shells 1602, 1604 that engage each other via respective advancement structures 1606, 1608 to advance the mandible. The upper and lower structures 1606, 1608 engage each other along anterior and posterior surfaces, respectively. Additionally, the upper structure 1606 includes an extended base portion 1610 that contacts and engages an upper surface 1612 of the lower structure 1608. In some embodiments, an upper magnetic element 1614 is positioned near the base portion 1610 and a lower magnetic element 1616 is positioned near the upper surface 1612, the attractive magnetic forces reversibly bias the structures 1606, 1608 towards the engaged configuration. This arrangement of magnetic elements can provide increased resistance to disengagement during mouth opening compared to other arrangements.

Figure 16B:
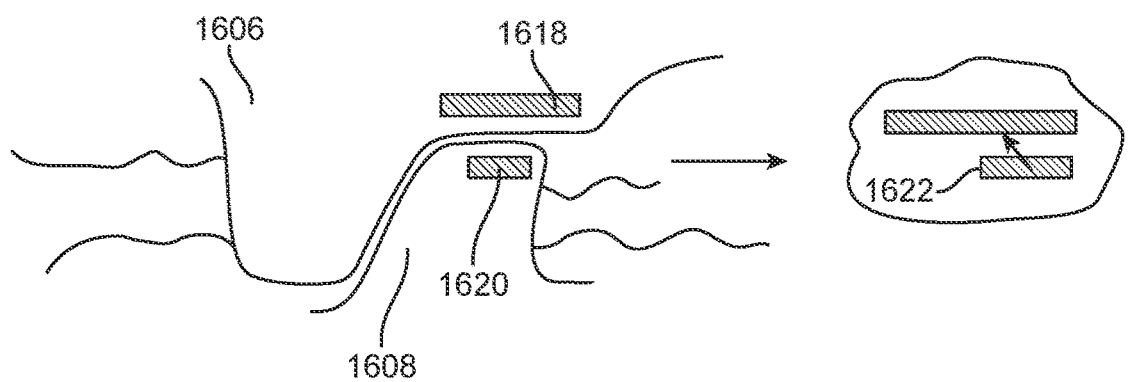
FIG. 16B illustrates a magnetic coupling with self-centering capabilities, in accordance with embodiments.

FIG. 16B illustrates a magnetic coupling with self-centering capabilities, in accordance with embodiments. The magnetic coupling is similar to that of FIG. 16A, except that the upper and lower magnetic elements 1618, 1620 have different lengths. In the depicted embodiment, the lower magnetic element 1620 is shorter than the upper magnetic element 1618, although it shall be appreciated that the lower element 1620 can be longer than the upper element 1618 in alternative embodiments. The self-centering tendencies of the magnetic elements 1618, 1620 can produce an attractive force having a posteriorly-directed component (see, e.g., arrow 1622), thus exerting a posterior force on the lower advancement structure 1608 that biases it towards the engaged position with the upper advancement structure 1606. This arrangement can further improve the stability of the engagement between the upper and lower advancement structures 1606, 1608.

Figure 16C:
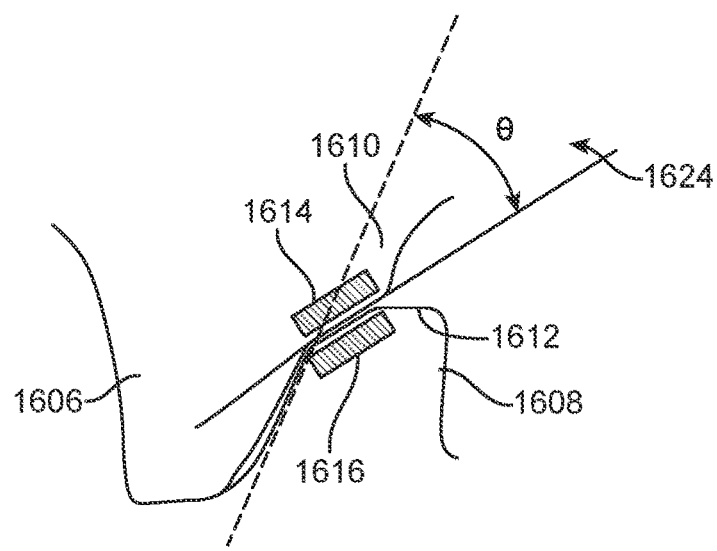
FIG. 16C illustrates adjustments to the geometry of a magnetic coupling, in accordance with embodiments.

FIG. 16C illustrates adjustments to the geometry of a magnetic coupling, in accordance with embodiments. The angle 1624 between the base portion 1610 and upper surface 1612 where the magnetic elements 1614, 1616 are located can influence the stability of the engagement between the upper and lower advancement structures 1606, 1608. For example, the angle 1624 can be adjusted to be approximately normal to the patient's mouth opening trajectory to facilitate disengagement during mouth opening movements.

Alternatively or in combination with the magnetic coupling mechanisms described herein, an intraoral appliance can utilize other types of coupling mechanisms to control the relative positioning of the jaws. For example, a mechanical coupling mechanism can include features shaped to mate with each other in order to promote advancement stability. Such features can include one or more of grooves, protrusions, receptacles, recesses, cavities, apertures, ribs, flanges, and the likes. The features can be arranged to mate when the advancement structures are engaged, thus reducing the likelihood of inadvertent disengagement. Additionally, the positioning of the features can be used to control the advanced configuration of the jaws, e.g., in terms of advancement position and vertical separation.

Figure 17A:
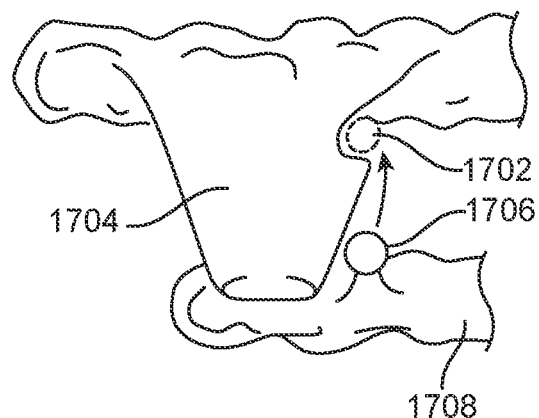
FIG. 17A illustrates a mechanical coupling for advancement structures comprising a cup and ball mechanism, in accordance with embodiments.

FIG. 17A illustrates a mechanical coupling for advancement structures comprising a cup and ball mechanism, in accordance with embodiments. In the embodiment of FIG. 17A, the appliance includes a first mating feature, e.g., a cup or detent 1702, formed on an engagement plane of an advancement structure 1704 and a second mating feature, e.g., a ball or rod 1706, on the other shell 1708. The second mating feature can engage the first mating feature, e.g., by seating in the cup or detent 1702 formed on the advancement structure 1704.

Figure 17B:
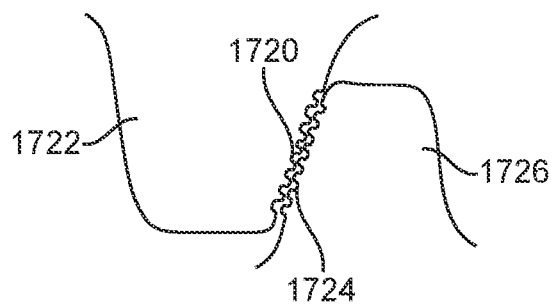
FIG. 17B illustrates a mechanical coupling for advancement structures comprising textured surfaces, in accordance with embodiments.

FIG. 17B illustrates a mechanical coupling for advancement structures comprising textured surfaces, in accordance with embodiments. In the embodiment of FIG. 17A, the appliance includes a first textured surface 1720 on a first advancement structure 1722 and a second textured surface 1724 on a second advancement structure 1726. The textured surfaces 1720, 1724 can include complementary features such as patterned grooves that mate with each other when the first and second advancement structures 1722, 1726 are engaged with each other.

Alternatively or in combination, the coupling mechanism can include fasteners, e.g., tethers, clasps, and the like, that constrain the movement of the advancement structures relative to each other. The fasteners can include some degree of compliance to accommodate small movements of the jaws while maintaining the overall advanced position of the mandible. In other embodiments, the fasteners can be relatively stiff so as to provide increased control over the relative positions of the advancement structures.

Figure 17C:
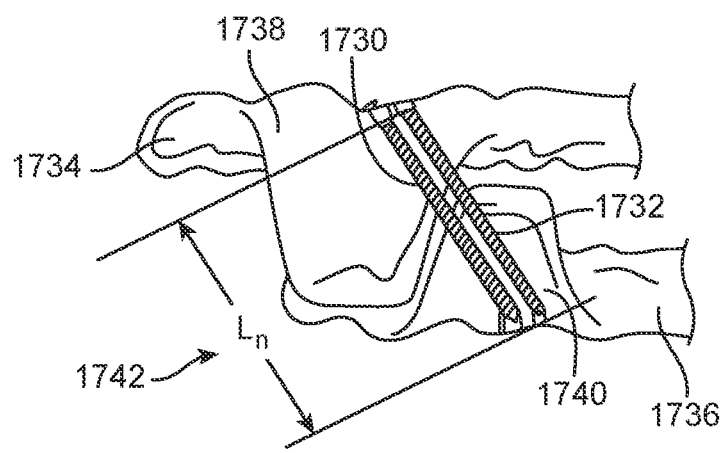
FIG. 17C illustrates elastic tethers for coupling advancement structures, in accordance with embodiments.

FIG. 17C illustrates elastic tethers 1730, 1732 for coupling advancement structures, in accordance with embodiments. Although FIG. 17C depicts a pair of tethers 1730, 1732, it shall be appreciated that the number of tethers can be varied as desired. Each elastic tether includes one end coupled to the upper shell 1734 and an opposing end coupled to the lower shell 1736. The positions and orientations of the elastic tethers 1734, 1736 can be varied as desired to control the resultant jaw configuration. For example, the end coupled to the upper shell 1734 can be positioned posteriorly relative to the end coupled to the lower shell 1736 such that the elastic forces in the elastic tether 1730, 1732 pull the upper and lower advancement structures 1738, 1740 into engagement with each other. In some embodiments, the tethers 1730, 1732 are arranged to be at their natural length 1742 (undeformed length) when the structures 1738, 1740 are correctly engaged. In other embodiments, the tethers 1730, 1732 are stretched longer than their natural length 1742 when the structures 1738, 1740 are engaged, such that tensile forces are applied to the structures 1738, 1740 in the engaged configuration.

Optionally, the intraoral appliances described herein can be configured to accommodate natural asymmetries in the patient's jaw configuration. In some embodiments, due to asymmetries in the neuromuscular and skeletal system of the jaw, the jaw advancement trajectory that is most comfortable for the patient may not necessarily be uniaxial (e.g., solely along the anterior-posterior axis). For example, the advanced position may include lateral translations or shifts (e.g., along a left-right direction), rotations (e.g., within a sagittal plane), or combinations thereof. Additionally, the comfortable advanced position may be influenced by asymmetrically stretched muscles.

Figure 24A:
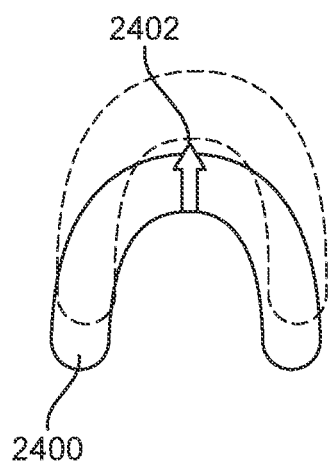
FIGS. 24A through 24C illustrate occlusal views of symmetric and asymmetric jaw advancement, in accordance with embodiments.
Figure 24B:
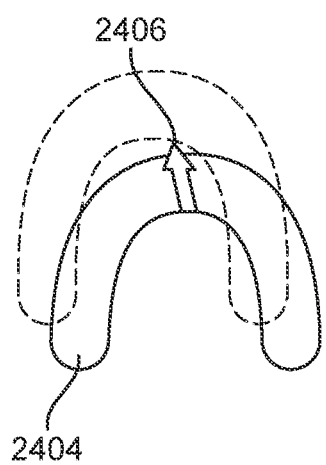
Figure 24C:
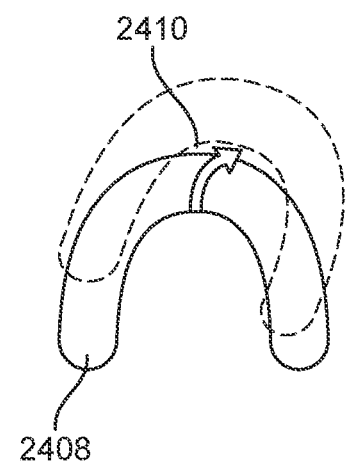

FIGS. 24A through 24C illustrate occlusal views of symmetric and asymmetric jaw advancement, in accordance with embodiments. FIG. 24A illustrates a symmetric advancement position in which the mandible 2400 is displaced solely in an anterior direction, as indicated by displacement vector 2402. FIG. 24B illustrates an asymmetric advancement position in which the mandible 2404 is displaced anteriorly with a lateral shift, as indicated by displacement vector 2406. FIG. 24C illustrates an asymmetric advancement position in which the mandible 2408 is rotated during advancement, as indicated by displacement vector 2410.

In embodiments where the patient's jaws exhibit natural asymmetries, a mandibular advancement appliance that produces uniaxial advancement may cause asymmetric stretching of the jaw muscles, which may lead to side effects such as jaw discomfort, muscle strain, TMJ dysfunction, and/or bite alterations. Accordingly, it can be beneficial to design advancement appliances that advance the mandible in a manner accommodating the asymmetries of the patient's anatomy. This can be achieved, for instance, by designing the position and/or geometries of the mandibular advancement structures to produce asymmetric advancement corresponding to the patient's natural jaw asymmetries.

Figure 25A:
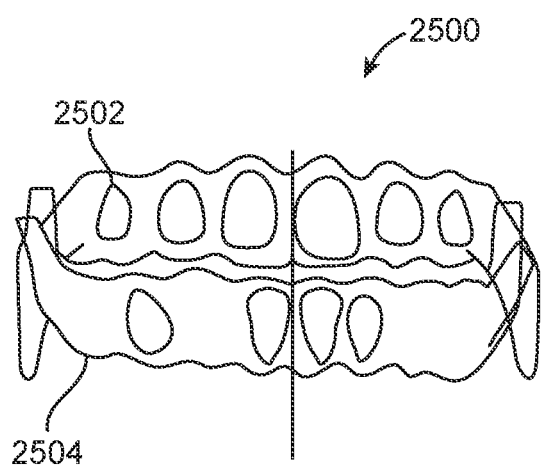
FIGS. 25A and 25B illustrate appliance design to accommodate a patient's jaw asymmetry, in accordance with embodiments.
Figure 25B:
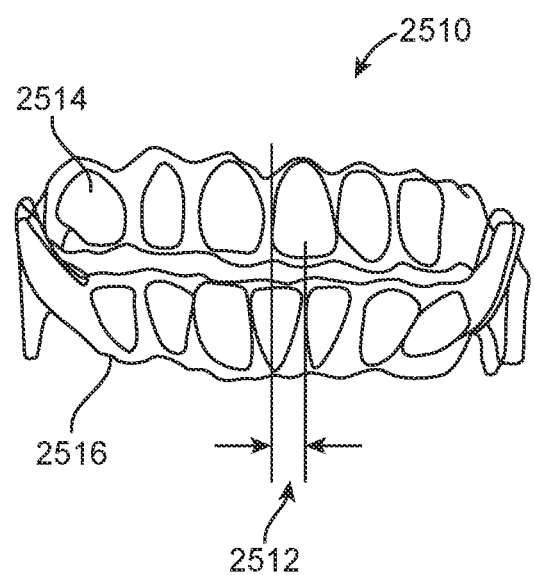

FIGS. 25A and 25B illustrate optimizing appliance design to accommodate a patient's jaw asymmetry, in accordance with embodiments. FIG. 25A illustrates a frontal view of an appliance 2500 which produces symmetric jaw advancement along the anterior-posterior axis, as indicated by alignment of the midlines of the upper shell 2502 and lower shell 2504. The mandible can be constrained to advance in a symmetric manner by the position and/or geometry of the advancement structures of the appliance 2500. FIG. 25B illustrates a frontal view of an appliance 2510 which produces asymmetric advancement, as indicated by a lateral shift 2512 between the midlines of the upper shell 2514 and lower shell 2516. This can be achieved, for instance, by designing the position and/or geometry of the advancement structures (e.g., depicted herein as fin-like structures on the buccal surfaces of the shells 2514, 2516) to allow for a lateral shift of the mandible as it is advanced relative to the maxilla. Alternatively or in combination, the advancement structures can be designed to place and/or constrain the mandible in a specified position (e.g., a position that is more comfortable for the patient). For example, the structures can include one or more lateral contact points to constrain lateral motion of the jaws. As another example, the positioning of the structures can be used to control the rotation of the mandible about the vertical axis.

In order to produce mandibular advancement devices that are customized to the patient, the appliance design and fabrication methods described herein may involve obtaining measurement data of the patient's jaw anatomy and/or jaw kinematics while the patient is awake. Alternatively, some or all of the measurement data described herein can be obtained while the patient is asleep, if desired. Various methods can be used to ensure the accuracy of such measurements. In some embodiments, digital scanning techniques are used to determine the spatial relationship between the patient's upper and lower jaws in a desired advanced position (e.g., while the patient is awake), and the appliance can be fabricated based on the spatial relationship data. For example, the patient's mandible jaw can be positioned and settled in a desired advanced position while the patient is awake (e.g., a position that is most comfortable and relaxed for the patient.) using a protrusion gauge. This can be facilitated, for instance, through the use of a physical device (e.g., retention materials, wax materials, and/or an adjustable 3-contact mechanism) to position the patient's jaw to a desired position. The patient's jaws can then be scanned while in the advanced position in order to measure the spatial relationship of the lower jaw with respect to the upper jaw while the patient is awake. In some embodiments, a physical device for positioning the patient's jaw may be relatively bulky and difficult to use with a scanner, unless a cone beam scanner or X-ray scanner is used to scan an image of the intraoral cavity. Alternatively or in combination, kinematic measurement data of the patient's jaws can be obtained, e.g., by placing reflective markers on certain locations on or near the jaws and performing digital scanning of the jaws at various advanced positions while is awake. In such embodiments, the kinematic measurement data can be mapped back to a model of the jaws (e.g., a skeletal model) in order to accurately predict the spatial relationship between the jaws at any advanced position.

Optionally, the design of the appliances provided herein (e.g., with respect to application, shape, position, size, etc. of the structures) can be dependent on various inputs. In some embodiments, the inputs are related to the patient's TMJ. For instance, if the patient has a TMJ disorder, oral appliance therapy may not be recommended in some situations. Alternatively, a force-limited appliance as discussed herein can be used for patients with TMJ disorders, e.g., an appliance configured to produce forces no greater than a physiological threshold that is appropriate for patients with TMJ disorder. In some embodiments, the appliance is designed to permit asymmetrical joint kinematics in order to accommodate natural and/or patient-specific TMJ asymmetries. For example, an appliance can include buccal structures (e.g., the advancement structures discussed with respect to FIG. 25B) shaped and/or placed to accommodate asymmetries associated with the TMJ. Various methods can be used to measure the patient's specific jaw asymmetry, including but not limited to facebow measurements, bite registrations, and/or ultrasound.

In some embodiments, the inputs for appliance design can include a targeted amount and/or maximum amount of anterior-posterior force to be exerted by the appliance. As described above and herein, a force measurement can be made for the patient in order to determine a patient-specific force threshold for the appliance. Optionally, the force system created by device activations can also be customized for the patient if a force measurement was taken.

Various embodiments of the intraoral appliances described herein can be provided as part of a mandibular advancement treatment for sleep apnea. In some embodiments, the present disclosure provides for patient-specific treatment of sleep apnea using customized mandibular advancement appliances. The appliances can be custom manufactured to fit a patient's dentition, typically by scanning or taking an impression of the patient's dentition to allow obtain precise tooth position data fabricating retainer-like upper and lower plates. Relying on the tooth data and mandibular protrusion and preferably with some knowledge of resulting anterior-posterior force, the appliances can be designed to apply force to the mandible while favorably distributing orthodontic forces applied to individual teeth which would result in unintended movement of the teeth relative to each other and the jaw. Exemplary appliances according to the present disclosure may produce no significant teeth movements. A patient-specific limiting protrusion can be designed into the device that is dependent on the anterior-posterior force generated by the mandibular protrusion in order to prevent adverse loading of the TMJ neuromuscular system.

Figure 18:
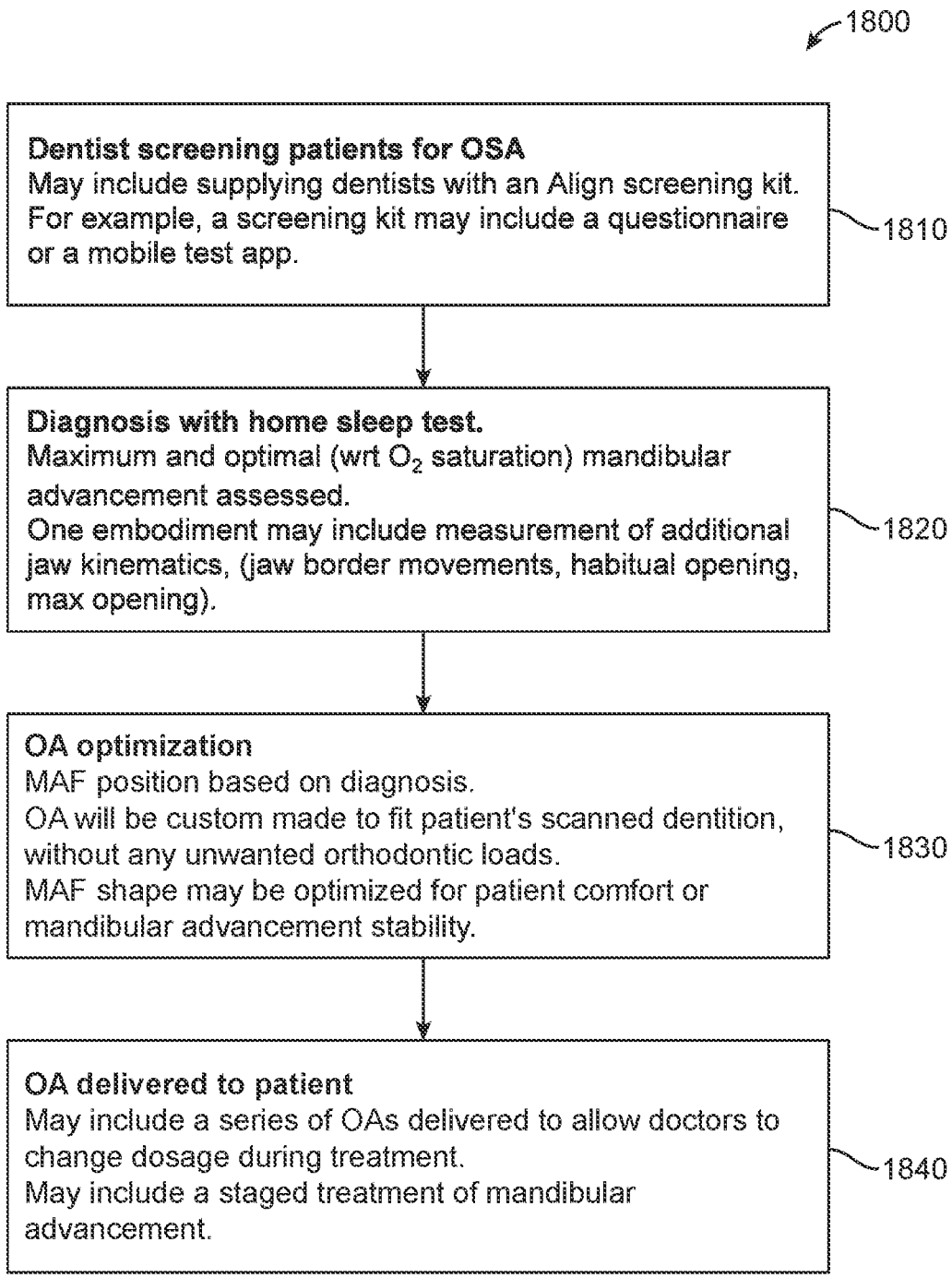
FIG. 18 illustrates a protocol for obtaining jaw kinematic data and optimizing patient treatment, in accordance with embodiments.

FIG. 18 illustrates a method 1800 for planning a mandibular advancement treatment, in accordance with embodiments. The method 1800 can be used in conjunction with any of the appliances described herein. One or more steps of the method 1800 can be performed by a treating professional, such as a dentist or orthodontist. At least some of the steps of the method 1800 can be implemented using digital treatment planning software, as described further herein.

In step 1810, the treating professional screens the patients for sleep apnea (e.g., OSA). Methods for performing sleep apnea screening are known to those of skill in the art. In some embodiments, the professional can be supplied with a screening kit that includes tools and/or guidance for performing the screening. For instance, a screening kit can include a questionnaire, mobile application for testing, screening software, or other such tools for facilitating evaluation of the patient's condition.

In step 1820, the patient is diagnosed with sleep apnea, e.g., using a home sleep test. The treating professional can obtain various types of data relevant to the patient's treatment, such as by assessing the maximum and/or optimal amount of mandibular advancement (e.g., with respect to oxygen saturation, restoration of normal airflow, etc.) for treating the sleep apnea. In some embodiments, additional measurement data such as jaw kinematic data (e.g., jaw border movements, habitual jaw opening, maximum jaw opening), jaw anatomy, force-displacement relationships, or data indicative of any of the patient-specific factors described herein can be obtained in step 1820.

In step 1830, one or more intraoral appliances for mandibular advancement are designed and optimized. The step 1830 can involve, for example, determining positioning and/or geometry of one or more mandibular advancement structures based on the diagnostic data obtained in steps 1810 and 1820. The positioning and/or geometry can be optimized for patient comfort, mandibular advancement stability, and/or mandibular advancement amount for effectively treating the sleep apnea, as described herein. Additionally, the intraoral appliance(s) can be custom made for the patient's specific teeth and jaw anatomy, e.g., based on measurement data such as scanning data of the dentition and/or jaws. In some embodiments, the intraoral appliance is designed to reduce or eliminate unwanted orthodontic loads that elicit undesirable tooth repositioning, as discussed herein.

In step 1840, the intraoral appliance is delivered to the patient. Optionally, the step 1840 can involve delivering a system of appliances, e.g., a set or series of appliances providing differing "dosages" of mandibular advancement, as described herein. For patients who require severe mandibular advancement, a staged advancement can be delivered, for instance, using the system of FIG. 12 for optimal treatment. For example, the lower two lower appliance shells 1214, 1216 might represent stages 1 and 2, respectively, of the treatment, with the other shells being used successively to achieved a targeted mandibular advancement while mitigating patient discomfort.

Although the above steps show method 1800 of planning a mandibular advancement treatment in accordance with embodiments, a person of ordinary skill in the art will recognize many variations based on the teaching described herein. Some of the steps may comprise sub-steps. Some of the steps can be combined with other steps. Many of the steps may be repeated as often as beneficial to the treatment. Some of the steps may be optional, such as one or more of steps 1810 or 1820. The order of the steps can be varied. For example, steps 1810 and 1820 may be performed in any suitable order.

In some embodiments, the mandibular advancement appliances described herein can also be used to reposition one or more teeth in accordance with an orthodontic treatment plan. For instance, an intraoral appliance can include cavity geometries shaped to receive one or more teeth and reposition the one or more teeth from an initial tooth arrangement towards a target tooth arrangement for the patient. Exemplary methods for designing and producing such appliances are described further herein. In some embodiments, some or all of the tooth-receiving cavities of a mandibular advancement appliance can include be shaped to reposition teeth to a target arrangement, while reducing or preventing unintentional tooth repositioning elicited by mandibular advancement as discussed herein. Optionally, some of the tooth-receiving cavities can be shaped to maintain a current arrangement of some of the patient's teeth, thus reducing or preventing any tooth repositioning of those teeth. For example, an appliance can include some cavities shaped to reposition a subset of teeth according to a treatment plan and some cavities shaped to maintain a different subset of teeth in their current positions and orientations. In alternative embodiments, all of the tooth-receiving cavities are shaped to maintain the patient's teeth in the current arrangement, such that the appliance serves as a retainer rather than a repositioning appliance.

In some embodiments, a mandibular advancement appliance can include tooth-receiving cavities that reposition one or more teeth towards a target arrangement in order to treat sleep apnea. Various types of orthodontic treatments for alleviating sleep apnea can be implemented in combination with the embodiments presented herein. For example, an orthodontic treatment plan can involve repositioning one or more teeth to increase the amount of space for the patient's tongue, such as one or more posterior teeth. Arch expansion of the posterior teeth to accommodate the volume of the tongue can allow the patient's tongue to move forward in the intraoral cavity, which may improve airflow and reduce obstruction of the air passages during sleep. Examples of posterior tooth movements that can be used to increase space for the tongue include but are not limited to tipping the crown in a buccal direction, translational movements in a buccal direction, and extrusion. In some embodiments, the movements of the posterior teeth result in leveling of the patient's curve of Spee (the curvature of the occlusal plane along the cusps of the teeth) which can increase the amount of room for the tongue. The tooth repositioning movements described herein can be applied to teeth of the lower jaw, upper jaw, or both jaws.

Figure 19A:
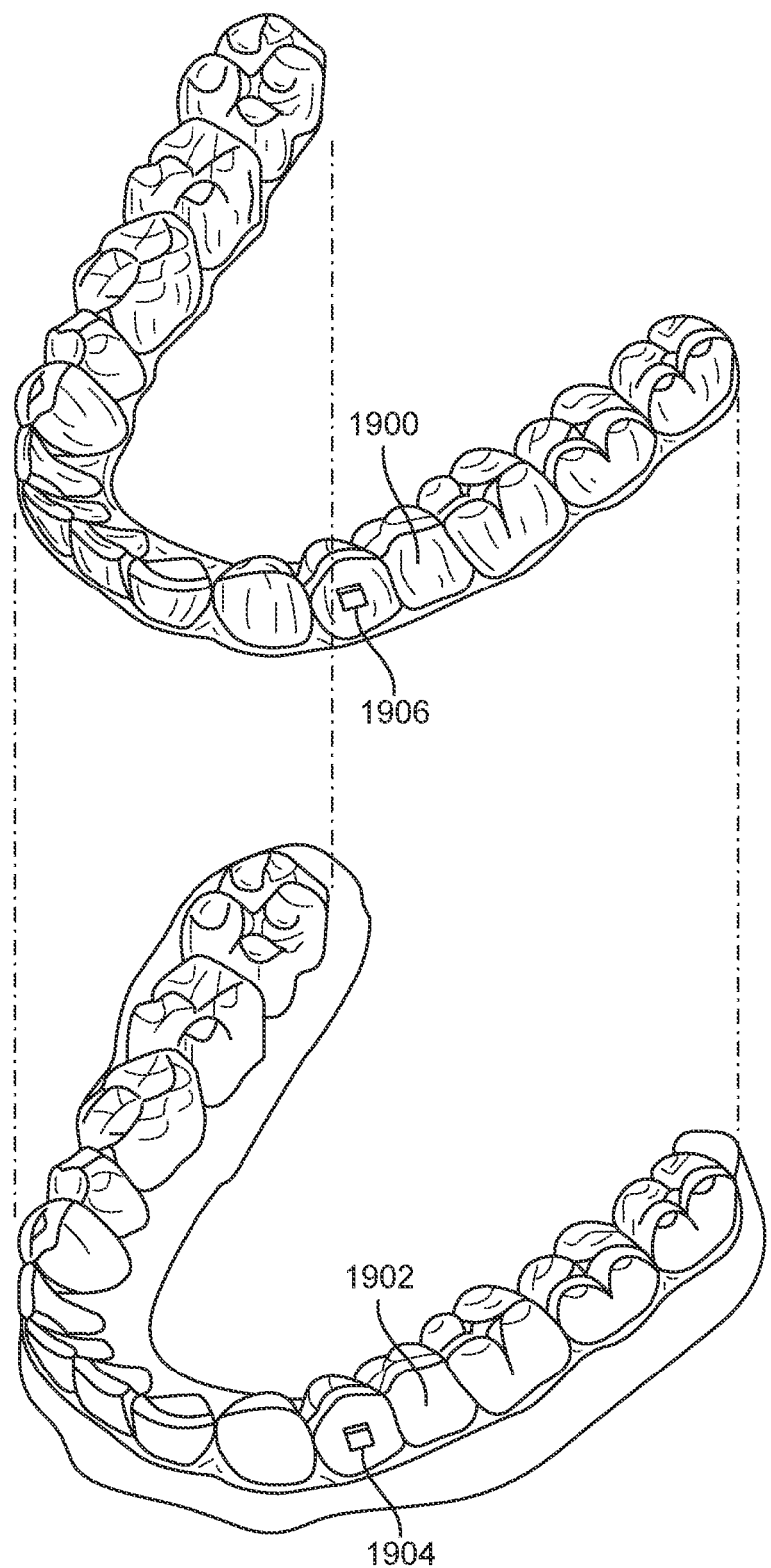
FIG. 19A illustrates a tooth repositioning appliance, in accordance with embodiments.

FIG. 19A illustrates an exemplary tooth repositioning appliance or aligner 1900 suitable for incorporation with the embodiments described herein. The appliance 1900 can be worn by a patient in order to achieve an incremental repositioning of individual teeth 1902 in the jaw. The appliance can include a shell (e.g., a continuous polymeric shell or a segmented shell) having teeth-receiving cavities that receive and resiliently reposition the teeth. In one embodiment, an appliance or portion(s) thereof may be indirectly fabricated using a physical model of teeth. For example, an appliance (e.g., polymeric appliance) can be formed using a physical model of teeth and a sheet of suitable layers of polymeric material. An appliance can fit over all teeth present in an upper or lower jaw, or less than all of the teeth. The appliance can be designed specifically to accommodate the teeth of the patient (e.g., the topography of the tooth-receiving cavities matches the topography of the patient's teeth), and may be fabricated based on positive or negative models of the patient's teeth generated by impression, scanning, and the like. Alternatively, the appliance can be a generic appliance configured to receive the teeth, but not necessarily shaped to match the topography of the patient's teeth. In some cases, only certain teeth received by an appliance will be repositioned by the appliance while other teeth can provide a base or anchor region for holding the appliance in place as it applies force against the tooth or teeth targeted for repositioning. In some cases, many or most, and even all, of the teeth will be repositioned at some point during treatment. Teeth that are moved can also serve as a base or anchor for holding the appliance as it is worn by the patient. Typically, no wires or other means will be provided for holding an appliance in place over the teeth. In some cases, however, it may be desirable or necessary to provide individual attachments or other anchoring elements 1904 on teeth 1902 with corresponding receptacles or apertures 1906 in the appliance 1900 so that the appliance can apply a selected force on the tooth. Exemplary appliances, including those utilized in the Invisalign® System, are described in numerous patents and patent applications assigned to Align Technology, Inc. including, for example, in U.S. Pat. Nos. 6,450,807, and 5,975,893, as well as on the company's website, which is accessible on the World Wide Web (see, e.g., the url "invisalign.com"). Examples of tooth-mounted attachments suitable for use with orthodontic appliances are also described in patents and patent applications assigned to Align Technology, Inc., including, for example, U.S. Pat. Nos. 6,309,215 and 6,830,450.

Figure 19B:
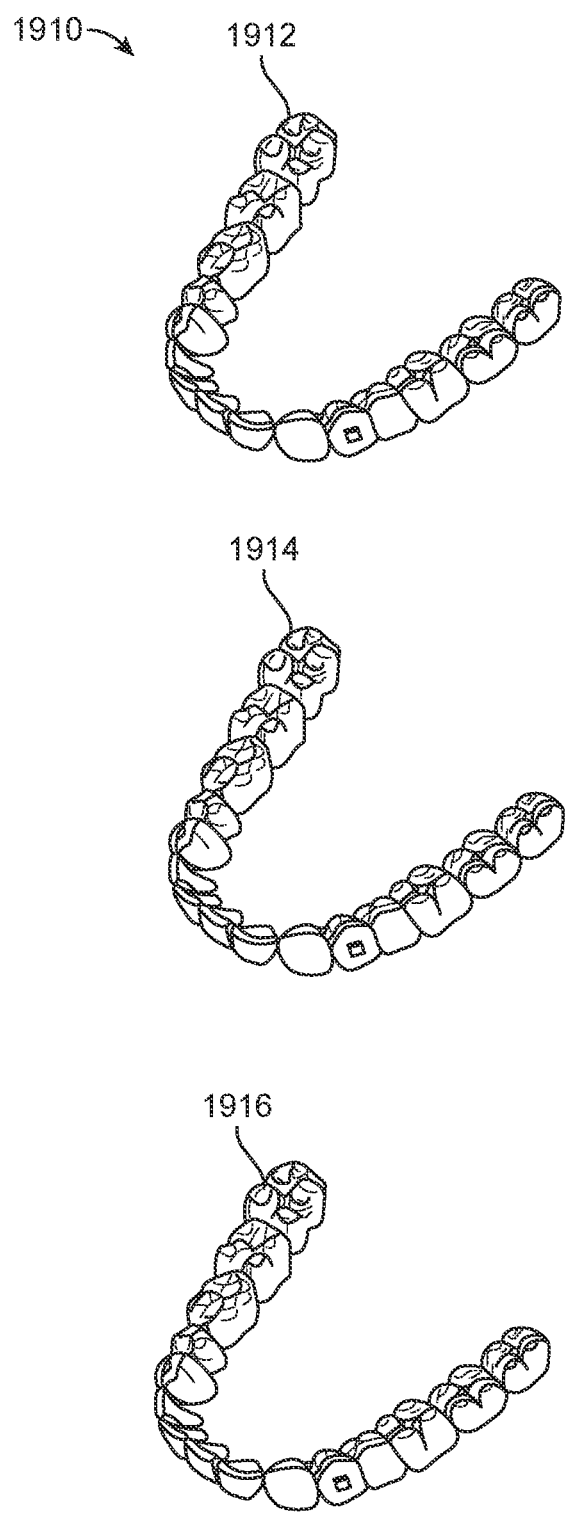
FIG. 19B illustrates a tooth repositioning system, in accordance with embodiments.

FIG. 19B illustrates a tooth repositioning system 1910 including a plurality of appliances 1912, 1914, 1916 suitable for incorporation with the embodiments provided herein. Any of the appliances described herein can be designed and/or provided as part of a set of a plurality of appliances used in a tooth repositioning system. Each appliance may be configured so a tooth-receiving cavity has a geometry corresponding to an intermediate or final tooth arrangement intended for the appliance. The patient's teeth can be progressively repositioned from an initial tooth arrangement to a target tooth arrangement by placing a series of incremental position adjustment appliances over the patient's teeth. For example, the tooth repositioning system 1910 can include a first appliance 1912 corresponding to an initial tooth arrangement, one or more intermediate appliances 1914 corresponding to one or more intermediate arrangements, and a final appliance 1916 corresponding to a target arrangement. A target tooth arrangement can be a planned final tooth arrangement selected for the patient's teeth at the end of all planned orthodontic treatment. Alternatively, a target arrangement can be one of many intermediate arrangements for the patient's teeth during the course of orthodontic treatment, which may include various different treatment scenarios, including, but not limited to, instances where surgery is recommended, where interproximal reduction (IPR) is appropriate, where a progress check is scheduled, where anchor placement is best, where palatal expansion is desirable, where restorative dentistry is involved (e.g., inlays, onlays, crowns, bridges, implant, veneers, and the like), etc. As such, it is understood that a target tooth arrangement can be any planned resulting arrangement for the patient's teeth that follows one or more incremental repositioning stages. Likewise, an initial tooth arrangement can be any initial arrangement for the patient's teeth that is followed by one or more incremental repositioning stages.

Figure 20:
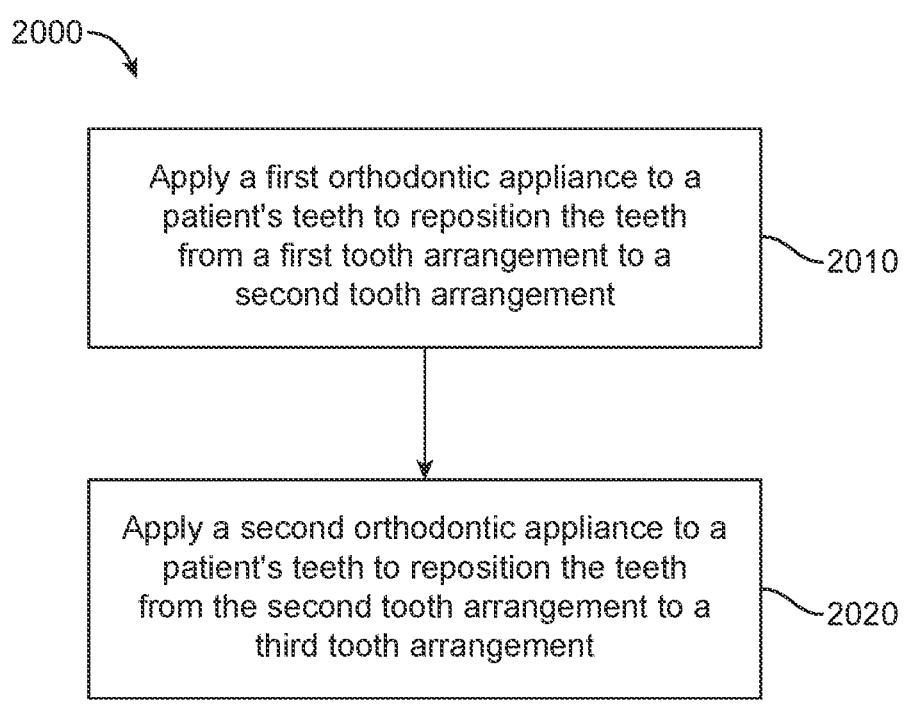
FIG. 20 illustrates a method of orthodontic treatment using a plurality of appliances, in accordance with embodiments.

FIG. 20 illustrates a method 2000 of orthodontic treatment using a plurality of appliances, in accordance with many embodiments. The method 2000 can be practiced using any of the appliances or appliance sets described herein. In step 2010, a first orthodontic appliance is applied to a patient's teeth in order to reposition the teeth from a first tooth arrangement to a second tooth arrangement. In step 2020, a second orthodontic appliance is applied to the patient's teeth in order to reposition the teeth from the second tooth arrangement to a third tooth arrangement. The method 2000 can be repeated as necessary using any suitable number and combination of sequential appliances in order to incrementally reposition the patient's teeth from an initial arrangement to a target arrangement. The appliances can be generated all at the same stage or in sets or batches (e.g., at the beginning of a stage of the treatment), or one at a time, and the patient can wear each appliance until the pressure of each appliance on the teeth can no longer be felt or until the maximum amount of expressed tooth movement for that given stage has been achieved. A plurality of different appliances (e.g., a set) can be designed and even fabricated prior to the patient wearing any appliance of the plurality. After wearing an appliance for an appropriate period of time, the patient can replace the current appliance with the next appliance in the series until no more appliances remain. The appliances are generally not affixed to the teeth and the patient may place and replace the appliances at any time during the procedure (e.g., patient-removable appliances). The final appliance or several appliances in the series may have a geometry or geometries selected to overcorrect the tooth arrangement. For instance, one or more appliances may have a geometry that would (if fully achieved) move individual teeth beyond the tooth arrangement that has been selected as the "final." Such over-correction may be desirable in order to offset potential relapse after the repositioning method has been terminated (e.g., permit movement of individual teeth back toward their pre-corrected positions). Over-correction may also be beneficial to speed the rate of correction (e.g., an appliance with a geometry that is positioned beyond a desired intermediate or final position may shift the individual teeth toward the position at a greater rate). In such cases, the use of an appliance can be terminated before the teeth reach the positions defined by the appliance. Furthermore, over-correction may be deliberately applied in order to compensate for any inaccuracies or limitations of the appliance.

Appliance fabrication or design can make use of one or more physical or digital representations of the patient's teeth. Representations of the patient's teeth can include representations of the patient's teeth in a current arrangement, and may further include representations of the patient's teeth repositioned in one or more treatment stages. Treatment stages can include a desired or target arrangement of the patient's teeth, such as a desired final arrangement of teeth. Treatment stages can also include one or more intermediate arrangements of teeth (e.g., planned intermediate arrangements) representing arrangements of the patient's teeth as the teeth progress from a first arrangement (e.g., initial arrangement) toward a second or desired arrangement (e.g., desired final arrangement).

Figure 21:
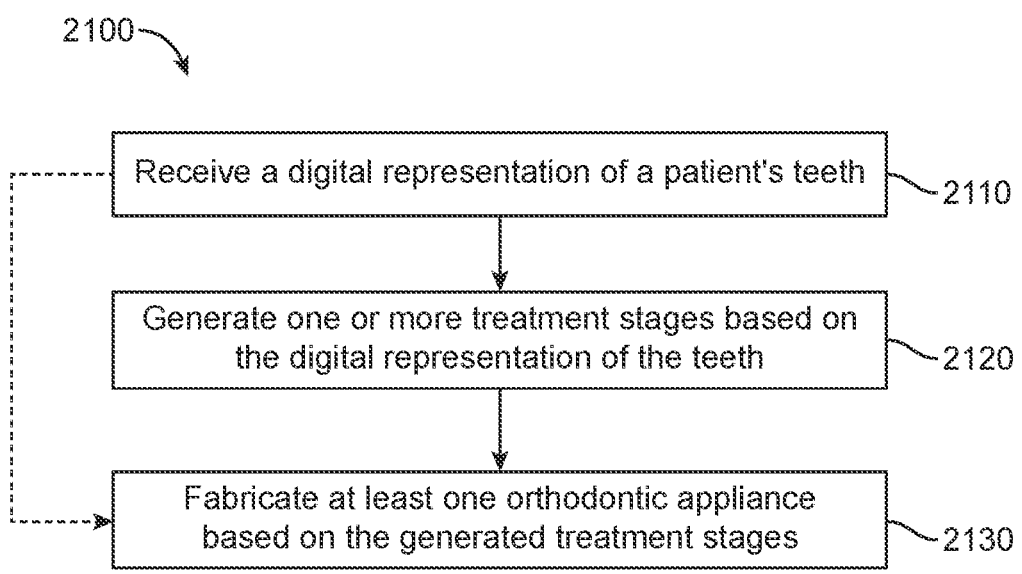
FIG. 21 illustrates a method for digitally planning an orthodontic treatment, in accordance with embodiments.

FIG. 21 illustrates a method 2100 for digitally planning an orthodontic treatment and/or design or fabrication of an appliance, in accordance with many embodiments. The method 2100 can be applied to any of the treatment procedures described herein and can be performed by any suitable data processing system.

In step 2110, a digital representation of a patient's teeth is received. The digital representation can include surface topography data for the patient's intraoral cavity (including teeth, gingival tissues, etc.). The surface topography data can be generated by directly scanning the intraoral cavity, a physical model (positive or negative) of the intraoral cavity, or an impression of the intraoral cavity, using a suitable scanning device (e.g., a handheld scanner, desktop scanner, etc.).

In step 2120, one or more treatment stages are generated based on the digital representation of the teeth. The treatment stages can be incremental repositioning stages of an orthodontic treatment procedure designed to move one or more of the patient's teeth from an initial tooth arrangement to a target arrangement. For example, the treatment stages can be generated by determining the initial tooth arrangement indicated by the digital representation, determining a target tooth arrangement, and determining movement paths of one or more teeth in the initial arrangement necessary to achieve the target tooth arrangement. The movement path can be optimized based on minimizing the total distance moved, preventing collisions between teeth, avoiding tooth movements that are more difficult to achieve, or any other suitable criteria.

In step 2130, at least one orthodontic appliance is fabricated based on the generated treatment stages. For example, a set of appliances can be fabricated to be sequentially worn by the patient to incrementally reposition the teeth from the initial arrangement to the target arrangement. Some of the appliances can be shaped to accommodate a tooth arrangement specified by one of the treatment stages. Alternatively or in combination, some of the appliances can be shaped to accommodate a tooth arrangement that is different from the target arrangement for the corresponding treatment stage. For example, as previously described herein, an appliance may have a geometry corresponding to an overcorrected tooth arrangement. Such an appliance may be used to ensure that a suitable amount of force is expressed on the teeth as they approach or attain their desired target positions for the treatment stage. As another example, an appliance can be designed in order to apply a specified force system on the teeth and may not have a geometry corresponding to any current or planned arrangement of the patient's teeth.

The appliance set may include one or more of the mandibular advancement appliances described herein. As discussed, the appliance can be designed to reduce or prevent unintentional tooth repositioning while including cavity geometries selected to elicit the tooth movements specified by the corresponding treatment stage. At least some of these properties can be determined via suitable computer software or other digital-based approaches. For example, computer modeling strategies can be used to determine suitable force systems including one or more forces and/or moments to be applied to the teeth in order to elicit the desired tooth movements and/or prevent unwanted movements, while producing a targeted amount of mandibular advancement. The geometry of the appliances (e.g., geometry of the shell, teeth receiving cavities, advancement structures, etc.) can be digitally designed based on the determined force systems. The digital models created using such methods may be used as input to a computer-controlled fabrication system for fabricating appliances.

As illustrated by the dashed line in FIG. 21, design and/or fabrication of an appliance, and perhaps a particular treatment plan, may include use of a representation of the patient's teeth (e.g., receive a digital representation of the patient's teeth 2110), followed by design and/or fabrication of an appliance based on a representation of the patient's teeth in the arrangement represented by the received representation.

Figure 22:
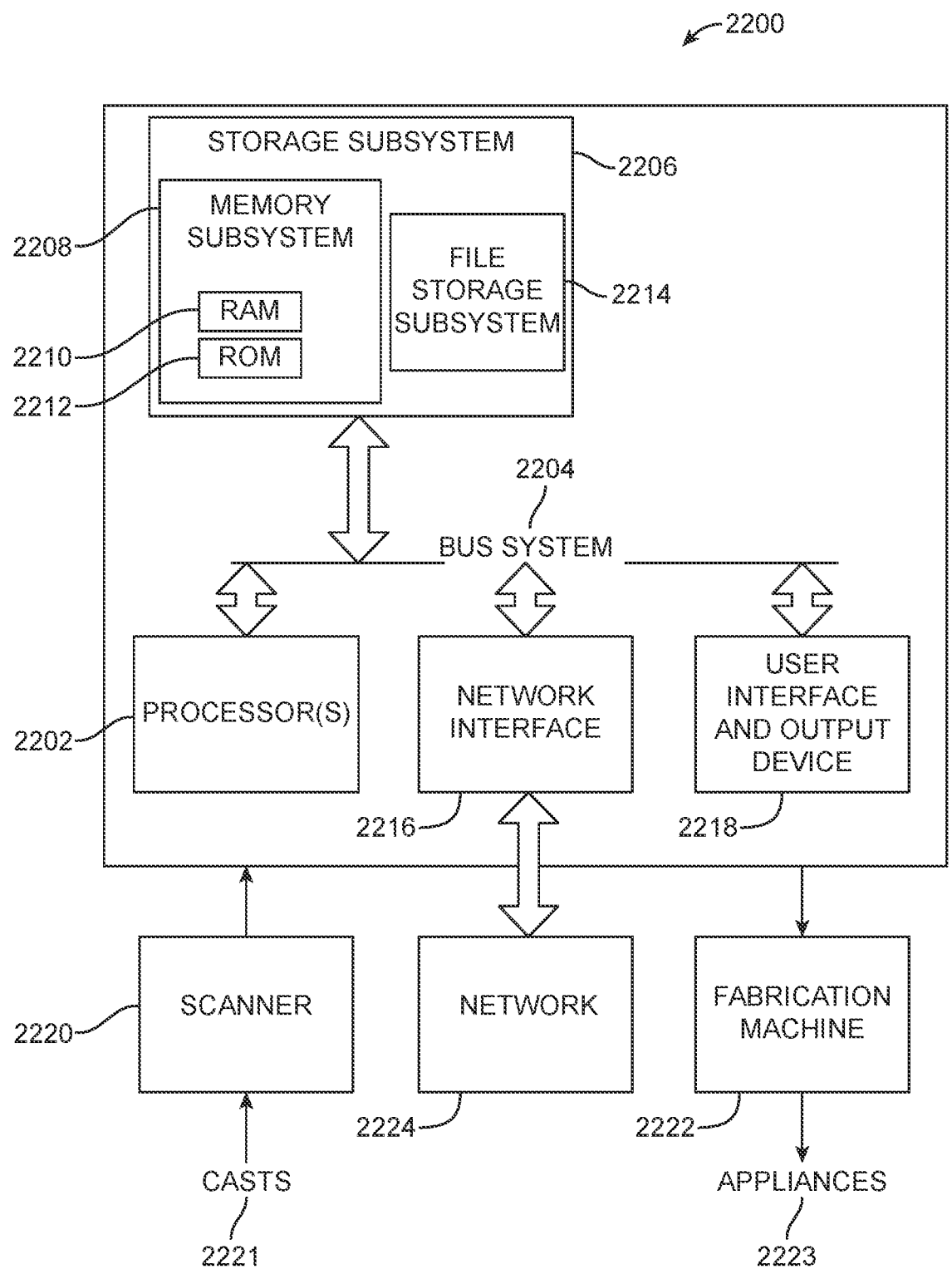
FIG. 22 is a simplified block diagram of a data processing system, in accordance with embodiments.

FIG. 22 is a simplified block diagram of a data processing system 2200 that may be used in executing methods and processes described herein. The data processing system 2200 typically includes at least one processor 2202 that communicates with one or more peripheral devices via bus subsystem 2204. These peripheral devices typically include a storage subsystem 2206 (memory subsystem 2208 and file storage subsystem 2214), a set of user interface input and output devices 2218, and an interface to outside networks 2216. This interface is shown schematically as "Network Interface" block 2216, and is coupled to corresponding interface devices in other data processing systems via communication network interface 2224. Data processing system 2200 can include, for example, one or more computers, such as a personal computer, workstation, mainframe, laptop, and the like.

The user interface input devices 2218 are not limited to any particular device, and can typically include, for example, a keyboard, pointing device, mouse, scanner, interactive displays, touchpad, joysticks, etc. Similarly, various user interface output devices can be employed in a system of the invention, and can include, for example, one or more of a printer, display (e.g., visual, non-visual) system/subsystem, controller, projection device, audio output, and the like.

Storage subsystem 2206 maintains the basic required programming, including computer readable media having instructions (e.g., operating instructions, etc.), and data constructs. The program modules discussed herein are typically stored in storage subsystem 2206. Storage subsystem 2206 typically includes memory subsystem 2208 and file storage subsystem 2214. Memory subsystem 2208 typically includes a number of memories (e.g., RAM 2210, ROM 2212, etc.) including computer readable memory for storage of fixed instructions, instructions and data during program execution, basic input/output system, etc. File storage subsystem 2214 provides persistent (non-volatile) storage for program and data files, and can include one or more removable or fixed drives or media, hard disk, floppy disk, CD-ROM, DVD, optical drives, and the like. One or more of the storage systems, drives, etc may be located at a remote location, such coupled via a server on a network or via the internet/World Wide Web. In this context, the term "bus subsystem" is used generically so as to include any mechanism for letting the various components and subsystems communicate with each other as intended and can include a variety of suitable components/systems that would be known or recognized as suitable for use therein. It will be recognized that various components of the system can be, but need not necessarily be at the same physical location, but could be connected via various local-area or wide-area network media, transmission systems, etc.

Scanner 2220 includes any means for obtaining a digital representation (e.g., images, surface topography data, etc.) of a patient's teeth (e.g., by scanning physical models of the teeth such as casts 2221, by scanning impressions taken of the teeth, or by directly scanning the intraoral cavity), which can be obtained either from the patient or from treating professional, such as an orthodontist, and includes means of providing the digital representation to data processing system 2200 for further processing. Scanner 2220 may be located at a location remote with respect to other components of the system and can communicate image data and/or information to data processing system 2200, for example, via a network interface 2224. Fabrication system 2222 fabricates appliances 2223 based on a treatment plan, including data set information received from data processing system 2200. Fabrication machine 2222 can, for example, be located at a remote location and receive data set information from data processing system 2200 via network interface 2224.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. Numerous different combinations of embodiments described herein are possible, and such combinations are considered part of the present disclosure. In addition, all features discussed in connection with any one embodiment herein can be readily adapted for use in other embodiments herein. It is intended that the following claims define the scope of the invention and that methods and structures within the scope of these claims and their equivalents be covered thereby.

What is claimed is:

1. A method for producing an intraoral appliance for treating sleep apnea in a patient, the method comprising:
   determining, with aid of one or more processors, a threshold force value for an amount of anterior-posterior force to be applied to the patient's teeth to displace the patient's lower jaw anteriorly relative to the patient's upper jaw; and
   determining, with aid of the one or more processors, a geometry for an intraoral appliance configured to displace the lower jaw anteriorly relative to the upper jaw when worn by the patient in order to treat the sleep apnea, wherein the intraoral appliance applies an amount of anterior-posterior force to the patient's teeth that is no greater than the threshold force value.

2. The method of claim 1, wherein the threshold force value is between about 0.5 N and about 20 N.

3. The method of claim 1, wherein the threshold force value is between about 20 N.

4. The method of claim 1, further comprising:
   receiving, with aid of the one or more processors, measurement data indicative of a patient-specific relationship between anterior displacement of the lower jaw relative to the upper jaw and anterior-posterior force applied to the patient's teeth.

5. The method of claim 4, further comprising:
   determining, with aid of one or more processors, a threshold displacement value for an amount of anterior displacement of the lower jaw relative to the upper jaw corresponding to the threshold force value.

6. The method of claim 4, wherein the intraoral appliance is configured to displace the lower jaw relative to the upper jaw by an amount no greater than the threshold displacement value.

7. The method of claim 1, wherein the threshold force value is less than an amount of anterior-posterior force that would cause unintended movements of the jaws or teeth.

8. The method of claim 1, further comprising:
   fabricating an appliance based on the geometry for the intraoral appliance.

9. The method of claim 1, wherein the intraoral appliance comprises a first shell shaped to couple with an upper arch of the patient and a second shell shaped to couple with a lower arch of the patient.

10. The method of claim 9, wherein the first shell comprises a first advancement structure and the second shell comprises a second advancement structure configured to engage with the first advancement structure to displace the lower jaw.

11. A system for producing an intraoral appliance for treating sleep apnea in a patient, the system comprising:
    one or more processors; and
    memory comprising instructions executable by the one or more processors to cause the system to at least:
    determine a threshold force value for an amount of anterior-posterior force that would be applied to the patient's teeth in order to displace the patient's lower jaw anteriorly relative to the patient's upper jaw, and
    determine a geometry for an intraoral appliance configured to displace the lower jaw anteriorly relative to the upper jaw when worn by the patient in order to treat the sleep apnea, wherein the intraoral appliance applies an amount of anterior-posterior force to the patient's teeth that is no greater than the threshold force value.

12. The system of claim 11, wherein the threshold force value is between about 0.5 N and about 20 N.

13. The system of claim 11, wherein the threshold force value is between about 20 N.

14. The system of claim 11, further comprising:
    receiving, with aid of the one or more processors, measurement data indicative of a patient-specific relationship between anterior displacement of the lower jaw relative to the upper jaw and anterior-posterior force applied to the patient's teeth.

15. The system of claim 14, further comprising:
    determining, with aid of one or more processors, a threshold displacement value for an amount of anterior displacement of the lower jaw relative to the upper jaw corresponding to the threshold force value.

16. The system of claim 14, wherein the intraoral appliance is configured to displace the lower jaw relative to the upper jaw by an amount no greater than the threshold displacement value.

17. The system of claim 11, wherein the threshold force value is less than an amount of anterior-posterior force that would cause unintended movements of the jaws or teeth.

18. The system of claim 11, further comprising:
    fabricating an appliance based on the geometry for the intraoral appliance.

19. The system of claim 11, wherein the intraoral appliance comprises a first shell shaped to couple with an upper arch of the patient and a second shell shaped to couple with a lower arch of the patient.

20. The system of claim 19, wherein the first shell comprises a first advancement structure and the second shell comprises a second advancement structure configured to engage with the first advancement structure to displace the lower jaw.

* * * * *